United States Patent [19]

Segalowitz

[11] Patent Number: 5,307,818
[45] Date of Patent: * May 3, 1994

[54] WIRELESS ELECTROCARDIOGRAPHIC AND MONITORING SYSTEM AND WIRELESS ELECTRODE ASSEMBLIES FOR SAME

[76] Inventor: Jacob Segalowitz, 505 S. Beverly Dr., Ste. 1240, Beverly Hills, Calif. 90212

[*] Notice: The portion of the term of this patent subsequent to Jan. 1, 2008 has been disclaimed.

[21] Appl. No.: 911,561

[22] Filed: Jul. 7, 1992

Related U.S. Application Data

[63] Continuation-in-part of Ser. No. 818,398, Jan. 2, 1992, abandoned, which is a continuation of Ser. No. 473,887, Feb. 7, 1990, abandoned, which is a continuation-in-part of Ser. No. 310,660, Feb. 15, 1989, Pat. No. 4,981,141.

[51] Int. Cl.$^5$ .......................................... A61B 5/0408
[52] U.S. Cl. .................................... 128/696; 128/903; 128/639
[58] Field of Search ............... 128/696, 903, 639, 640, 128/641, 644; 364/413.06

[56] References Cited

U.S. PATENT DOCUMENTS

| | | | |
|---|---|---|---|
| 2,298,125 | 10/1942 | Hartman | 128/2.1 |
| 2,660,165 | 11/1953 | Miller | 128/2.06 |
| 3,409,007 | 11/1968 | Fuller | 128/644 |
| 3,757,778 | 9/1973 | Graham | 128/2.06 |
| 3,848,582 | 11/1974 | Milani | 128/2.06 |
| 3,858,576 | 1/1975 | Dehnert | 128/2.06 |
| 3,882,277 | 5/1975 | DePedro | 172/2 DP |
| 3,908,641 | 9/1975 | Judson | 128/2.06 |
| 3,986,498 | 10/1976 | Lewis | 128/696 |
| 4,121,573 | 10/1978 | Crovella et al. | 128/2.1 |
| 4,121,575 | 10/1978 | Mills et al. | 128/644 |
| 4,141,351 | 2/1979 | James | 128/696 |
| 4,202,344 | 5/1980 | Mills et al. | 128/644 |
| 4,233,987 | 11/1980 | Feingold | 128/639 |
| 4,319,241 | 3/1982 | Mount | 128/903 |
| 4,328,814 | 5/1982 | Arkans | 128/640 |
| 4,353,372 | 10/1982 | Ayer | 128/640 |
| 4,356,486 | 10/1982 | Mount | 340/870.38 |
| 4,522,211 | 6/1985 | Bare et al. | 128/640 |

(List continued on next page.)

FOREIGN PATENT DOCUMENTS

| | | | |
|---|---|---|---|
| 00109 | 4/1987 | Australia | A61B 5/04 |
| 212278 | 3/1987 | European Pat. Off. | 128/696 |
| 293560 | 9/1953 | Switzerland | 128/696 |

OTHER PUBLICATIONS

Webster, J. G.; "Electrocardiographic Monitors"; Sections Diagnostic Electrocardiographic Devices and Electrocardiographic Monitoring Devices; pp. 1002–1017.

Primary Examiner—William E. Kamm
Assistant Examiner—George Manuel
Attorney, Agent, or Firm—Flehr, Hohbach, Test, Albritton & Herbert

[57] ABSTRACT

A precordial strip assembly for use on a patient having skin, right and left arms and legs and a heart with a precordium lying thereover comprising an elongate strip having first and second surfaces. Six conductive contact elements identified as $V_1$ through $V_6$ are mounted in spaced apart positions along the length of the strip. In other embodiments, conductive contact elements identified as LA, LL and RA can be mounted on the strip. A reference contact element can be carried by the strip for serving as a common reference for each of the conductive contact elements. The contact elements are exposed on the first surface of the strip and are adapted to contact the patient's skin for detecting heart signals from the patient when the precordial strip assembly is placed on the precordium of the patient. Junction means is carried in a single region by the strip and is electrically connected to the contact elements. One or more microchips can be connected to the contact elements for transmitting a radio frequency signal which carries the heart signals detected by the contact elements.

72 Claims, 14 Drawing Sheets

U.S. PATENT DOCUMENTS

| | | | |
|---|---|---|---|
| 4,583,549 | 4/1986 | Manoli | 128/640 |
| 4,593,284 | 6/1986 | Clifford | 340/870.18 |
| 4,606,352 | 8/1986 | Geddes | 128/702 |
| 4,622,979 | 11/1986 | Katchis | 128/702 |
| 4,658,831 | 4/1987 | Reinhard | 128/697 |
| 4,675,656 | 6/1987 | Narcisse | 340/539 |
| 4,742,831 | 5/1988 | Silvian | 128/710 |
| 4,763,660 | 8/1988 | Kroll et al. | 128/640 |
| 4,784,162 | 11/1988 | Ricks | 128/903 |
| 4,827,943 | 5/1989 | Bornn | 128/668 |
| 4,852,572 | 8/1989 | Nakahashi et al. | 128/640 |
| 4,854,323 | 8/1989 | Rubin | 128/644 |
| 4,957,109 | 9/1990 | Groeger et al. | 128/696 |
| 4,966,154 | 10/1990 | Cooper et al. | 128/671 |
| 4,981,141 | 1/1991 | Segalowitz | 128/696 |
| 5,042,481 | 8/1991 | Suzuki et al. | 128/639 |
| 5,153,584 | 10/1992 | Engira | 128/903 |
| 5,184,620 | 2/1993 | Cudahy et al. | 128/639 |
| 5,191,886 | 3/1993 | Paeth et al. | 128/640 |

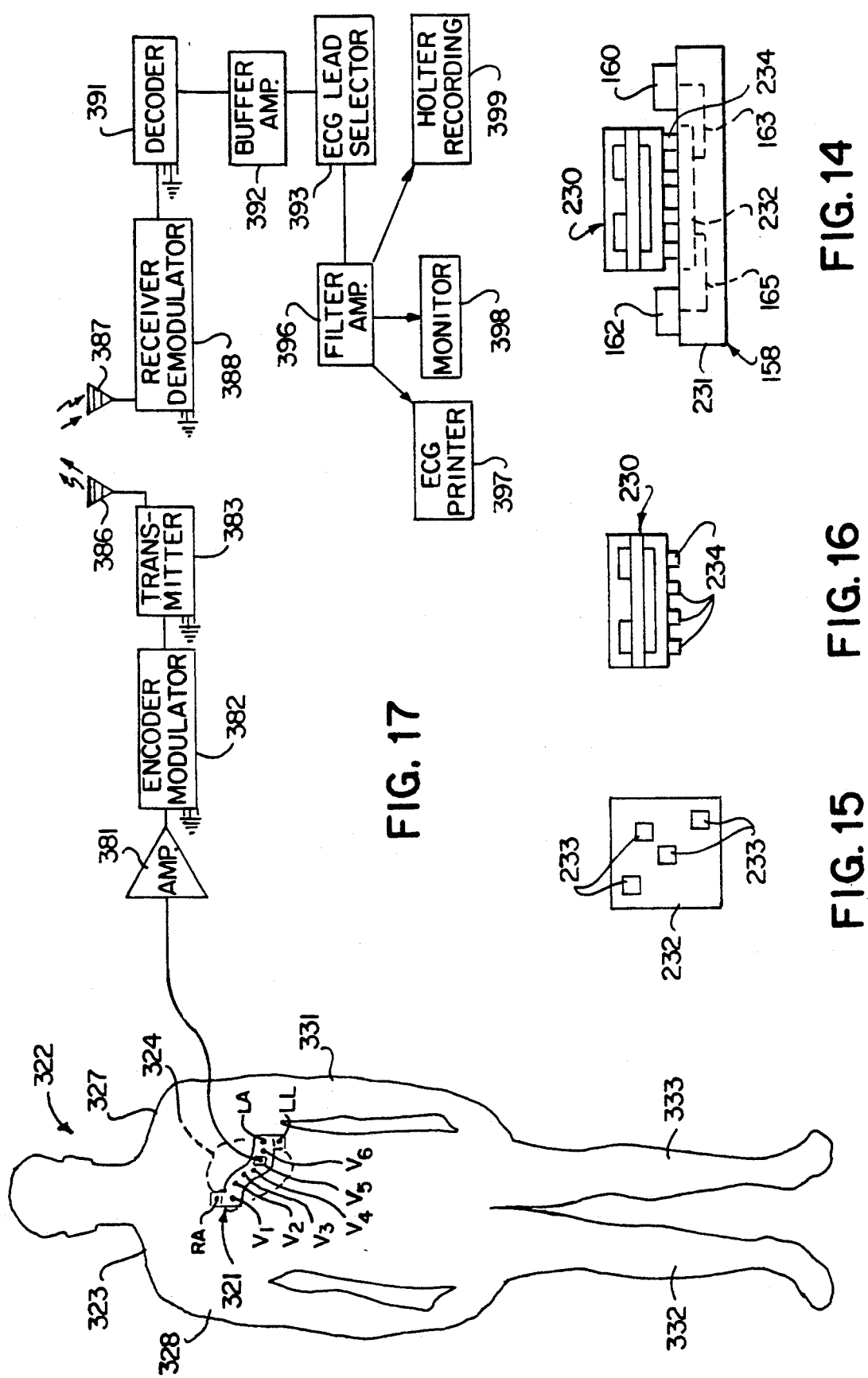

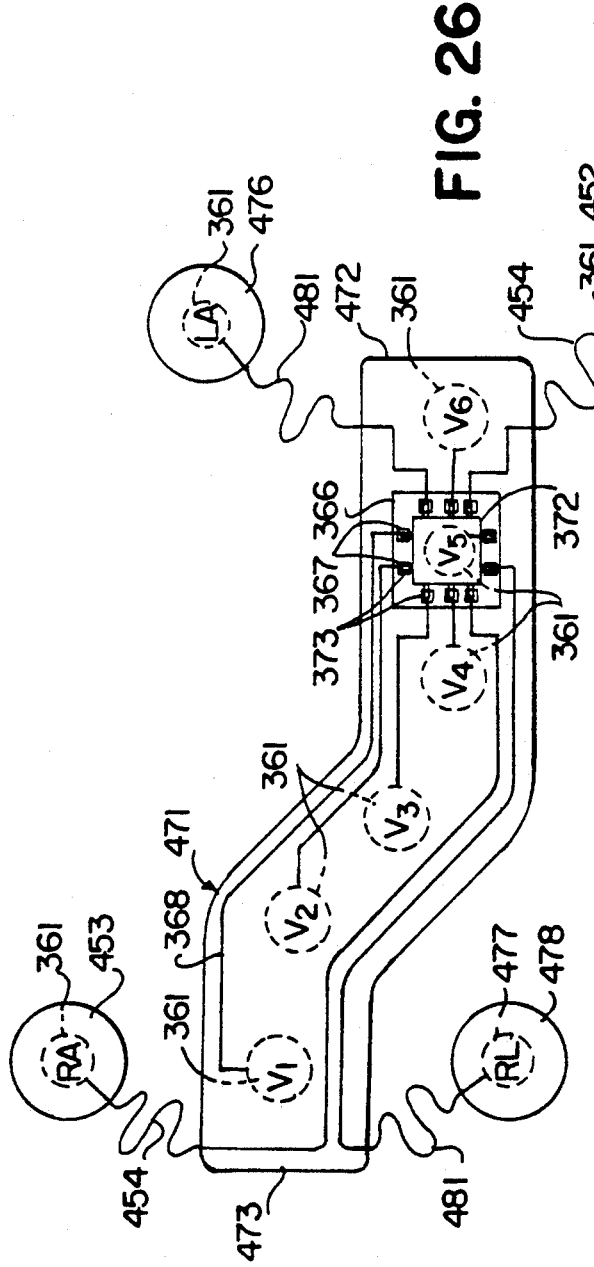
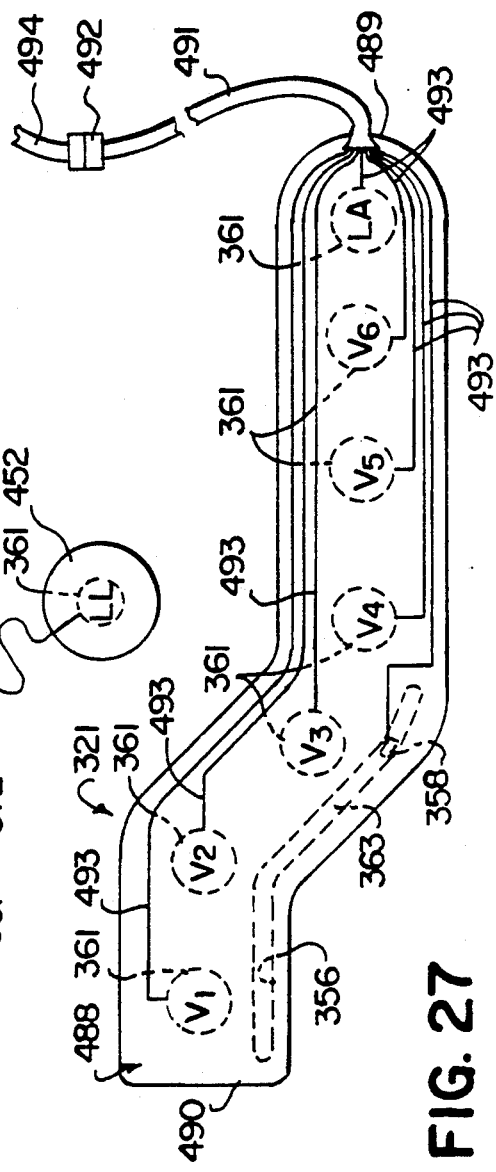
FIG. 26
FIG. 27

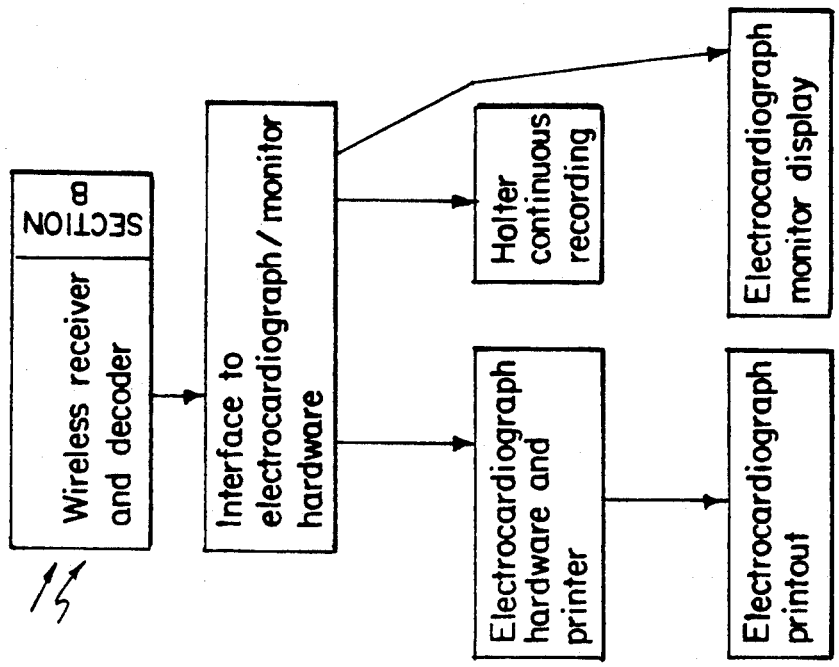
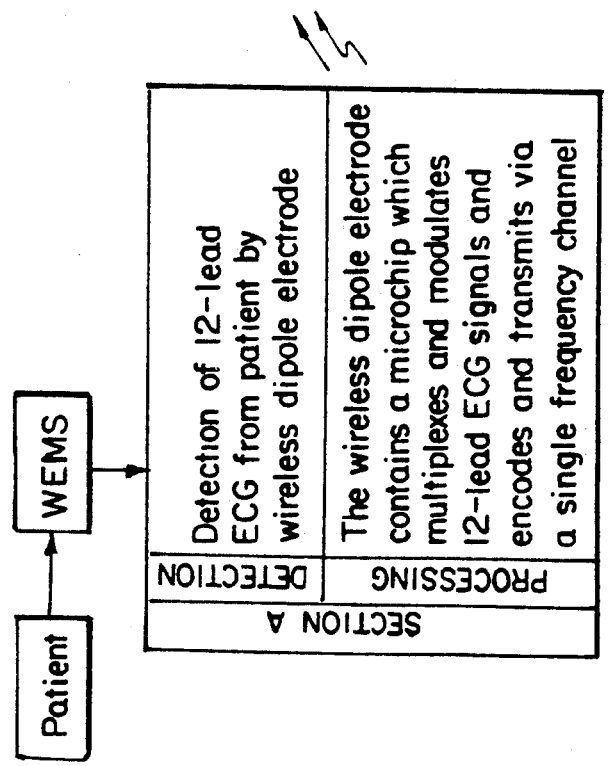
FIG. 28

WIRELESS ELECTROCARDIOGRAPHIC AND MONITORING SYSTEM AND WIRELESS ELECTRODE ASSEMBLIES FOR SAME

CROSS-REFERENCES TO RELATED APPLICATIONS

This application is a continuation-in-part of U.S. Ser. No. 07/818,398, Jan. 2, 1992, abandoned, which is a continuation of U.S. Ser. No. 07/473,887, Feb. 7, 1990, abandoned, which is a continuation-in-part of U.S. Ser. No. 07/310,660, Feb. 15, 1989, U.S. Pat. No. 4,981,141.

BACKGROUND OF THE INVENTION

1. Field of the Invention

This invention relates to medical instrumentation and a method and system for the use thereof and, more particularly, to electrocardiographic and cardiocirculatory monitoring equipment and a method and system relating thereto.

2. Prior Art

Every muscle can perform only one movement, the shortening of its fibers by contraction. This also applies to the heart muscle. Every action of a muscle has associated with it an electrical activity which changes in the course of the contraction. The electrical signal thus associated with the muscle action is transmitted through various tissues and ultimately reaches the surface of the body whereupon such electrical signals can be detected by electrodes applied to the skin. Thus, such signals that are being detected by the electrodes can be recorded with the aid of suitable electrocardiographic equipment or can be observed in or recorded with a monitor/recording unit. The record thus obtained is called an electrocardiogram or a rhythm-monitoring strip.

As early as 1855 action currents from the heart were recorded as measurements were being made of a beating frog heart. The first actual recording of a frog electrocardiogram was made by A. D. Waller in 1887. The first recording of a human heart electrical action signal (hereinafter "heart-signal") was made by A. D. Waller in 1889. Modern electrocardiography, however, started with Einthoven (credited with the bipolar lead triangle setting for recordings of standard limb leads I, II and III), who invented the string galvanometer and applied it to recording small voltages of short duration, which is the category into which heart-signals fall. His recording techniques have not been improved upon very much since they were first published many years ago. Here it should be noted that the term "lead" as used herein is being used in the medical sense and not the electronic sense (i.e., "lead" is a spatial position at which the heart-signal is viewed, not a wire).

After Einthoven's work, the entire field of research stagnated for nearly thirty years until the introduction by Wilson of upper and lower extremities' local leads and the zero electrode used in unipolar recordings.

The entire twelve-lead system is fed by unipolar and bipolar signals. Unipolar leads are divided into unipolar extremity or limb leads and unipolar precordial or chest leads.

In the unipolar lead system, the limb leads are:
aVR—the unipolar right arm lead, (R designating the right arm);
aVL—unipolar left arm lead, (L designating the left arm); and
aVF—unipolar left leg lead.

In all of these limb leads, the "a" stands for "augmented". The unipolar chest leads are designated by the letter "V" followed by a subscript numeral which represents the exact location on the chest. In a standard electrocardiographic setting there are six precordial leads, $V_1$-$V_6$.

In the unipolar lead system, the potential differences are measured between each of the electrodes that are placed on the right arm, left arm, left leg, and precordial points $V_1$-$V_6$ on the chest and a common reference point consisting of an electrode on the right leg. Each of the lead electrodes is independently considered as an active point compared to the common reference electrode (point) on the right leg, and is measured in relation to that common reference electrode.

In standard bipolar leads, lead I is the potential difference between the arms, i.e., the left arm potential minus the right arm potential. Lead II is the potential difference between the left leg potential and the right arm potential. Lead III is the potential difference between the left leg and the left arm. If the leads are diagrammed on the body they inscribe, essentially, an equilateral triangle. The polarity of these widely-separated bipoles was arbitrarily determined many years ago in order to record upright electrical deflections in these three limbs leads in most normal objects. The electrocardiograph generates the lead voltages from the potentials applied to it from the electrodes. The term "lead" as used in electrocardiography means view of the heart's electrical impulse. That view varies among leads.

The electrocardiograph is widely used by the medical profession. The standard electrocardiograph requires at least ten wires which are attached to the body of the patient at one end and to the electrocardiograph at the other end to detect heart-signals and transform them into a twelve-lead electrocardiogram evaluation. This involves attaching six electrodes to the chest or precordial area to obtain recordings of leads $V_1$-$V_6$ as well as attaching four electrodes to the arms and legs of the patient to obtain recordings of leads I, II, III, aVR, aVL and aVF. (For heart rhythm monitoring, only three electrodes and three terminal wires are applied to the chest.) After the ten electrodes are attached to the patient, ten specific wires must be connected between each specific electrocardiograph terminal and the related electrode of the predetermined position.

In electrocardiographic terminology, the terms "dipole", "bipole" and "unipolar" have different meanings and applications. The "single dipole" concept is used to represent the local spread of excitation over cardiac tissue as recorded by a single recording electrode. This local excitation is in the form of a local influx and/or outflux of electrically charged elements, referred to as ions, through the cell membrane. The term "equivalent dipole" has been a term used since the days of Einthoven to represent the theoretical "electrical center" of a volume conductor used to describe the progression, magnitude and location of the electrical activity of the human body. This "equivalent dipole" has both direction and magnitude at any instance in the cardiac cycle and is traditionally represented as a vector that points in the direction of the positive pole of a dipole having both positive and negative poles. The vector has a length proportional to the magnitude of the dipoles' potential difference (i.e., the potential difference between its positive and negative poles).

The term "bipolar" has several uses in clinical electrocardiography and electrophysiology. Bipolar endocardial and epicardial recordings refer to recordings made between a cathode and anode of a recording device which are relatively closely spaced (e.g., several millimeters to one centimeter). For example, bipolar cardiac recordings are taken by modern pacemakers having leads that are reasonably closely spaced. In surface electrocardiographic practice, bipolar lead systems, as discussed above, are defined as limb lead systems that measure the potential differences between the three limb electrodes on the right and left arms and the left leg. The term "unipolar" is used in the practice of surface electrocardiography as described above.

The conventional and currently existing electrocardiographic systems are limited in operation. An early manifestation of acute myocardial ischemia is the development of ST-segment and T-wave changes. Clinical decisions for treatment are based on ST-segment shifts on the surface electrocardiogram. ST-segment depression is believed to represent subendocardial involvement, with less extensive myocardial injury. ST-segment elevation reflects transmural involvement, with greater extent of myocardial injury. Currently existing electrocardiographic monitoring equipment in the coronary intensive care units (CICU) and intensive care units (ICU) provides single-lead arrhythmia monitoring of cardiac events which is unable to detect myocardial ischemia in real time occurrence.

In the surgical setting, the cardiac catheterization laboratory protocol of percutaneous transluminal coronary angioplasty (PTCA) procedures employs the use of three-lead arrhythmia monitoring which is unable to detect ischemic events during actual performance of percutaneous transluminal coronary angioplasty.

In the ambulatory setting, Holter monitoring provides only arrhythmia recording and detection, which is unable to identify or locate coronary silent ischemia. Transtelephonic electrocardiogram transmission currently employs single-lead arrhythmia monitoring which is unable to identify or locate myocardial ischemic events in patients who have undergone percutaneous transluminal coronary angioplasty procedures, coronary artery bypass graft (CABG) surgery, or are currently being treated with antiarrhythmic drugs or are experiencing stable angina pectoris episodes.

In other settings, existing protocols employ single-lead electrocardiographic monitoring in the coronary intensive care mobil unit and emergency room, thereby permitting arrhythmia monitoring only. As can be seen, current coronary care electrocardiographic monitoring techniques are aimed at detection of cardiac arrhythmias rather than myocardial ischemia.

Existing electrocardiographic systems are also limited in diagnosing myocardial ischemia after noncardiac surgery. Patients undergoing noncardiac surgery sometimes have postoperative cardiac events. Adverse cardiac events are a major cause of morbidity and mortality after such surgery. It is necessary to determine the predictors of these outcomes in order to focus efforts on prevention and treatment. It would be helpful to know which patients are at highest risk. Clinical experience has demonstrated that postoperative myocardial ischemia during the first 48 hours after surgery confers a nearly threefold increase in the odds of having an adverse cardiac outcome and, more importantly, a ninefold increase in the odds of having an ischemic event (cardiac death, nonfatal myocardial infarction or unstable angina) in patients undergoing noncardiac surgery. In some clinical studies, postoperative myocardial ischemia was prevalent, occurring in more than 40 percent of the patients, and was silent in nearly all cases studied.

In addition, many and frequent difficulties are associated with the practical operation of the conventional and currently existing electrocardiographic systems due to the following factors:

1. The need to connect predetermined specific wires to predetermined specific electrodes (e.g. defined limb and side to defined wire, as well as specific precordial points to defined precordial wires) is time-consuming. In addition, connection errors are relatively frequent.

2. The wires often need to be untangled, resulting in the loss of precious time.

3. Existing electrocardiographic systems are somewhat impractical for use in coronary intensive care mobile units where speed of operation is critical.

4. Wire defects and damage are difficult to detect.

5. During many surgical procedures, single lead arrhythmia monitoring wires extend beneath the sterile surgical field. These wires often become disconnected from the electrodes and can interrupt the surgical procedure. In addition, existing electrocardiographic systems do not permit myocardial ischemia detection during surgery.

6. Patients in intermediate coronary care units sometimes disconnect the signal carrying wires from the electrocardiographic monitor while ambulating. By doing so, cardiac rhythm monitoring is interrupted.

7. Current electrocardiographic monitoring is limited in range and distance by the proximity between the patient and the electrocardiograph or monitor.

8. Current percutaneous transluminal coronary angioplasty (PTCA), diagnostic heart catheterization and other invasive interventional procedures performed in the cardiac catheterization suite; electrocardiographic monitorings in coronary intensive care units, intensive care unit (ICU) and coronary intensive care mobile units; and thrombolytic therapy monitoring; in each case, employ single lead or three lead electrocardiographic detection which provides only arrhythmia monitoring and is unable to diagnose myocardial ischemic events.

9. Patient compliance with the procedures and requirements of current electrocardiographic systems is minimal.

Therefore, it is an object of this invention to overcome the problems previously experienced in connection with the application of electrocardiographs in the taking of electrocardiograms and in connection with the rhythm monitoring of patients.

Another object of this invention is to provide an electrocardiographic and monitoring system in which the physical wires between the patient and the electrocardiograph or monitor are eliminated.

Another object of this invention is to provide an electrocardiographic and monitoring system in which a reduced standard number of wireless electrodes provide a complete standard twelve-lead electrocardiogram.

Another object of the present invention is to provide a precordial strip assembly containing a plurality of conductive elements for placement on the precordium area of a patient.

Another object of the invention is to provide a precordial strip assembly containing a reference conductive element permitting elimination of the standard right leg reference electrode.

Another object of the invention is to provide a precordial strip assembly having RA and LL conductive elements positionable on the patient in a position remote from the $V_1$ through $V_6$ and LA conductive elements.

Another object of the invention is to provide a self contained precordial strip assembly for detecting and transmitting heart signals.

SUMMARY OF THE INVENTION

In accordance with the preferred embodiments of the present invention there is disclosed a two-section medical monitoring system. One section includes the electrodes that are affixed to the patient for detection of and/or analysis of specific electrical signals and the second section is the receiving equipment for analyzing the signals. No wires extend between the two sections. The second section interfaces with the electrocardiograph or electrocardiographic monitoring equipment. Each wireless electrode operates independently of all of the other electrodes and is self-contained and self-powered and individually radiates its measured signal to a corresponding individual receiver in the monitoring equipment section. To ensure that the receivers in the monitoring-receiving section operate on the proper signal from the electrodes, each of the electrodes transmits its signal with an encoded pattern that can be decoded only by its corresponding receiver in the monitoring unit. Additionally, in one embodiment of the present invention, one of the electrodes to be connected to the patient includes a receiver, and the monitoring unit contains a corresponding transmitter which is also encoded to prevent the receiver from operating on the wrong signal.

The present invention also presents several different configurations, or groupings, of the ten electrodes needed for a "complete" standard twelve-lead electrocardiogram (ECG) monitoring. By grouping the electrodes, while maintaining their individual proper function, the number of appliances that have to be affixed to the patient is reduced, thus reducing the amount of time necessary to apply the electrodes and further minimizing the chance of error from the installation of the electrodes in the wrong locations on the patient.

The electrocardiac activity information detected and transmitted by the system conforms to all professional standards and levels of accuracy for vector progression, duration, intensity, and form characteristics specifically with respect to the following features:

1. Rhythm
2. Rate
3. P wave
4. P-R interval
5. QRS interval
6. QRS complex
7. ST segment
8. T wave
9. U wave
10. Q-T duration The system will function within a nominal range of approximately 50 meters between the electrode system and the monitoring-receiving unit. This configuration is suitable for operation with either a single-channel or a multi-channel electrocardiograph, monitor, or Holter. Each of those units may be fixed or portable, battery or AC powered. The receiving-demodulating-decoding base unit of the system of the present invention can be connected to existing stand-alone electrocardiographs or, by reason of its miniature size, can be integrated into new generations of such machines. Interference between multiple systems operating in the same facility is prevented by choosing different center frequencies for each of the transmitters and corresponding receivers within the corresponding system and all other systems within 100 meters or more of each other.

The dipole electrodes may be circular with concentric outer ring and center skin contacts, the outer ring being the reference potential contact to the body of the patient. Alternatively, an electrode with contacts that are spaced-apart from each other may be used, one being the signal or pick-up contact, and the other being the reference or zero potential contact.

While reference has been made herein to a radio frequency (RF) system of coupling between body electrodes and the monitoring-receiving base unit, it should be understood that with only minor changes in the circuitry and the proper operating environment, ultrasonic or semiconductor transmission techniques as well as other technologies may be used.

In one embodiment, the unipolar, the left arm, right arm, and left leg limb signals are fed to a bridge or "Wilson" network in the base unit to derive a reference signal for application to the right leg reference or indifferent electrode. That reference signal is used to modulate a frequency modulation (FM) transmitter at the base unit. At the right leg electrode a battery operated receiver detects, decodes, and amplifies the indifferent or reference signal and applies it to the right leg through a two-contact electrode to complete the signal path in the system. Alternatively, a balanced, mixed combination of the left arm, right arm, and left leg signals is radiated from the base unit to the right leg RF receiver electrode which applies such combination signal to the right leg.

Referring to bipolar lead recordings, the electrodes function in the same wireless fashion with the switchable characteristic of each electrode permitting identification of the location of that electrode so that the proper combination of limb signals is utilized in the ECG to develop I, II, and III leads.

Similarly, the precordial electrodes $V_1$-$V_6$, according to this invention, are coupled in wireless fashion to appropriate, respective channels in the base station for processing and use.

In other embodiments of the present invention the electrode on the right leg and the associated receiver and the corresponding transmitter in the base unit have been eliminated to further reduce the number of electrode assemblies that must be placed on the patient. Further reduction in electrode assemblies can be made by using a strip on which all of the precordial electrodes are mounted.

The precordial strip assembly of the present invention is for use on a patient having skin, right and left arms and legs and a heart with a precordium lying thereover. The assembly includes an elongate strip with first and second surfaces. Six conductive contact elements identified as $V_1$ through $V_6$ are mounted in spaced apart positions along the length of the strip. In other embodiments, conductive contact elements identified as LA, LL and RA can be mounted on the strip. A reference contact element can be carried by the strip for serving as a common reference for each of the conductive contact elements. The contact elements are exposed on the first surface of the strip and are adapted to contact the patient's skin for detecting heart signals from the patient when the precordial strip assembly is placed on the precordium of the patient. Junction means is carried in a single region by the strip and is electrically connected to the contact elements. One or more microchips can be connected to the contact elements for transmitting a radio frequency signal which carries the heart signals detected by the contact elements.

BRIEF DESCRIPTION OF THE DRAWING

This invention and its advances over the prior art can best be understood by reading the Specification which follows in conjunction with the drawing herein, in which:

FIG. 14 is a side elevational view of another embodiment of a dipole electrode structure, similar to the dipole electrode structure shown in FIG. 6, of the present invention.

FIG. 15 is a top plan view of a portion of the dipole electrode structure shown in FIG. 14.

FIG. 16 is a side elevational view of a portion of the dipole electrode structure shown in FIG. 14.

FIG. 17 is a view of another embodiment of a precordial strip assembly for electrocardiographic monitoring placed on the precordium area of a patient, together with a block diagram of a wireless electrocardiographic monitoring system.

FIG. 26 is a top plan view of another embodiment of a precordial strip incorporating the present invention.

FIG. 27 is a top plan view of yet another embodiment of a precordial strip incorporating the present invention.

FIG. 28 is a block diagram of a wireless electrocardiographic monitoring system which incorporates the present invention.

DETAILED DESCRIPTION OF THE PREFERRED EMBODIMENTS

In this application, the terms "unipolar" and "bipolar" are used in the traditional electrocardiographic sense, that is denoting measurements between electrode pairs relating to the appropriate limbs and having the conventional polarity, thereby yielding conventional electrocardiographic wave-forms during cardiac excitation. The term "dipolar" recording, however, is used in this application in a novel way, and refers to the new method and electrode concept in which the three electrodes in the wireless three electrode system configuration, as well as the single patch-electrode in the wireless single electrode system configuration, are comprised of both a positive and a negative terminal (pole), thereby obviating the need for a right leg grounding terminal as the reference point (reference electrode). Both above mentioned wireless system configurations enable recording of complete standard twelve-lead electrocardiograms. The "dipolar electrode" concept is completely different from the traditional "bipolar recording" obtained from the limb leads of standard electrocardiography machines currently available for clinical use.

Figures 1, 1A:
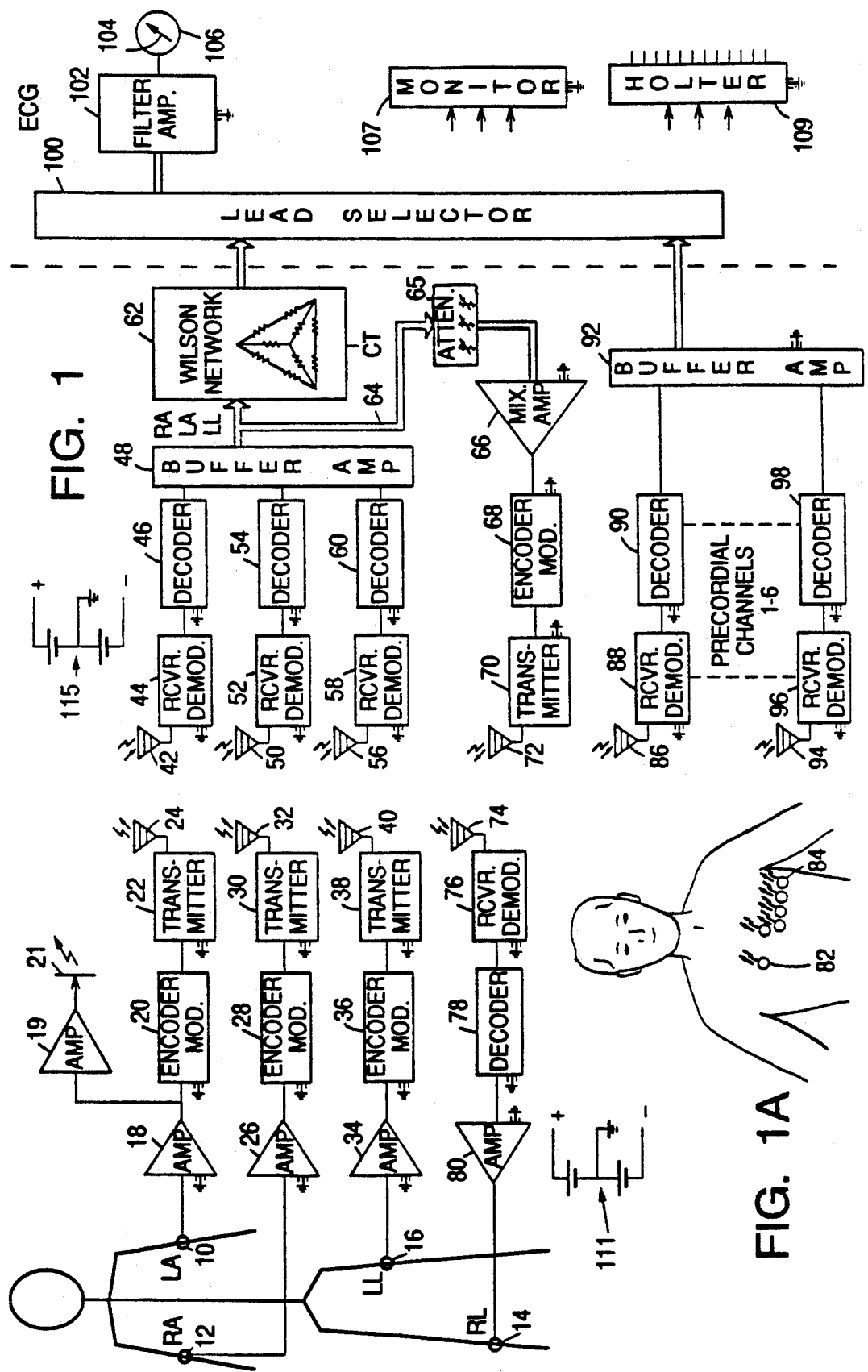
FIG. 1 is a block diagram of a wireless electrocardiograph system according to one embodiment of the present invention.
FIG. 1A is a graphical representation of the distribution of additional electrodes in the system of FIG. 1.

FIG. 1 shows a first embodiment of the present invention. In FIG. 1, the human body is represented by a stick figure to show the location of limb electrodes of the system. Electrode 10 is connected to the left arm, electrode 12 is connected to the right arm, electrode 14 is connected to the right leg, and electrode 16 is connected to the left leg. Each of these electrodes requires two contactive surfaces which come into contact with the patient. They may be of either the concentric type shown in FIG. 2 or of the spaced-apart type of FIG. 6. In the FIG. 2 type the outer conductive strip is used to establish a localized zero or reference potential, and the center connector is the source of signal for transmission or the point of application of the signal in the receiving mode. The outer ring may be referred to as an indifferent electrode of a localized nature. In the FIG. 6 type, one contact is the signal contact, and the other contact is the reference or indifferent electrode.

The output signal from electrode 10 is fed to amplifier 18 which feeds encoder-modulator 20. The signal thus derived is used to modulate transmitter 22 which is connected to antenna 24 from which the modulated RF signal is radiated. Amplifier 18 may comprise a microchip-type RC 4560 which has a dual-stage operational amplifier. Encoder-modulator 20 may comprise a CM 8555 IPA, or the equivalent, in combination with a 4OH393 chip. If digital encoding is utilized, a single transmitting frequency may be used for all transmitters. However, if analog modulation by the signal from electrode 10 is utilized, encoder-modulator 20 may act merely as a modulator, and each of the transmitters may be set at a different center frequency. Transmitter 22, and corresponding transmitters in other channels, may comprise a 93OF5 microchip which includes a Colpitts oscillator. The audio frequency range which must be reproduced by the system is 0.05 Hz to 125 Hz. The FM swing of the carrier frequency is typically no higher than 40 percent of the carrier frequency.

As shown, the output signal of amplifier 18 may also be fed through an additional amplifier 19 to an LED 21 which will give a light pulse each time a heart-signal is received at electrode 10. This heart-signal indicator may be provided at each electrode if desired.

The heart-signal from electrode 12 is fed to an amplifier 26 which, again, is a high gain, low noise amplifier, and the output signal of amplifier 26 is fed to encoder-modulator 28 and then to transmitter 30. The output signal of transmitter 30 is fed to antenna 32 for radiation.

The heart-signal from left leg electrode 16 is fed to amplifier 34, and the output signal of amplifier 34 is fed to encoder-modulator 36 for modulating FM transmitter 38. The output signal of transmitter 38 is fed to antenna 40 for radiation.

The signal radiated by antenna 24 is intercepted by antenna 42 and fed to receiver-demodulator 44, the output signal of which is fed to decoder 46 and then to buffer amplifier 48.

The signal from antenna 32 is intercepted by antenna 50 and fed to receiver-demodulator 52, the output signal of which is fed to decoder 54 and then to buffer amplifier 48.

Similarly, the signal from antenna 40 is received by antenna 56, and that signal is demodulated in receiver-demodulator 58 which feeds its output signal to decoder 60 for application to buffer amplifier bank 48. It should be understood that in buffer amplifier bank 48 there is a series of amplifiers, one for each transmitting limb signal channel. The signals from buffer amplifier 48 are fed to what is known as a "Wilson" network. This is essentially a bridge, the make up of which can be seen in FIG. 3. The left arm, right arm, and left leg signals are coupled to the "Wilson" network to produce what is known as an indifferent or reference potential which appears at the central terminal (CT). In this embodiment the signal at CT is not used, but it is used in the embodiment of FIG. 4. Instead, here, the right arm, left arm, and left leg signals are fed to a balancing attenuator 65 (three independently variable impedance paths) and then to a mixer amplifier 66 where the mixed signal is amplified by an internal low noise, high gain amplifier. The output signal of mixer amplifier 66 is applied to encoder-modulator 68 to generate the signal to modulate transmitter 70 which is coupled to antenna 72 for radiation by antenna 72. The radiated reference signal is picked up by receiving antenna 74, such antenna being coupled to receiver-demodulator 76 which develops a signal in the audible or sub-audible frequency range. Such signal, if it is encoded, may then be decoded by decoder 78, and the resulting signal may be applied to amplifier 80 which is coupled to the active contact of electrode 14 carried by the right leg. This establishes the so-called zero potential on the indifferent or reference electrode 14. Such a zero signal can be used for operation of a system involving the use of unipolar limb leads. The signals from the same electrodes are used to produce the bipolar limb leads previously described.

Figure 5:
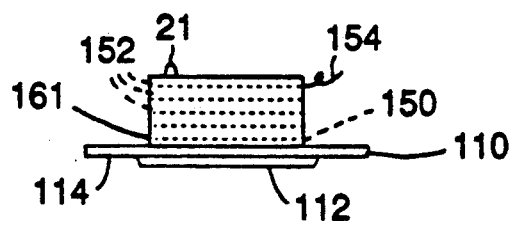
FIG. 5 is an elevational view of the concentric electrode of FIG. 2.
Figure 12A:
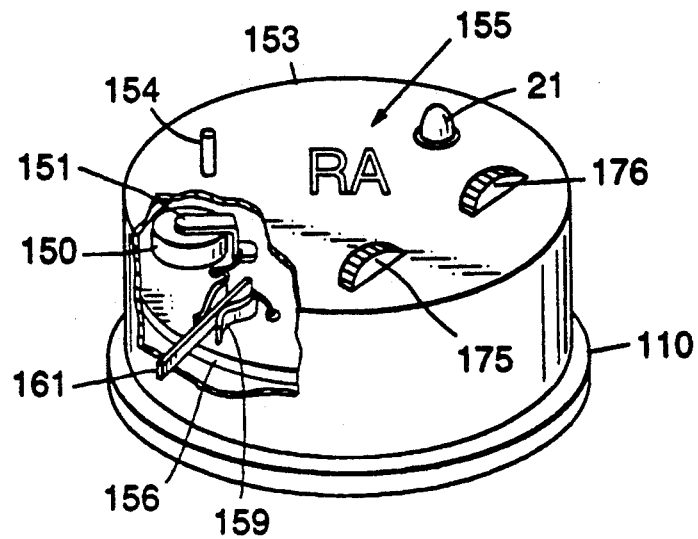
FIG. 12A is a partial cut-away perspective view of a transmitter/electrode assembly of the present invention.
Figure 12B:
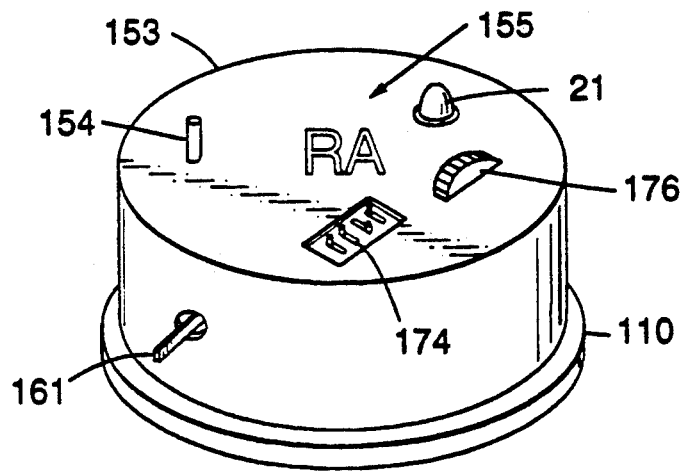
FIG. 12B is a perspective view of a transmitter/electrode assembly of the present invention.

The transmitters in the system, if purely analog techniques are involved, may be set at center frequencies of, for example, 72.080 MHz and at multiples of 160 KHz around that center frequency. Since the transmitters operate simultaneously with 160 KHz separation between their center frequencies there is no problem with intermodulation at the respective receivers, each of which has a corresponding detector center frequency so that the proper received signal is acted upon. Operation at much higher frequencies, for example, in the 400 MHz band, results in a much shorter antenna requirement but increases power requirements, thus putting a heavier load on the very small battery which can be mounted with the microchips in connection with the electrodes utilized in the system, as shown in FIGS. 5, 12A, and 12B. This analysis applies equally to electrodes used to detect signals for unipolar or bipolar leads. With a digitally encoded system, the center frequency may also be changed between systems to reduce the possibility of interference between systems operating in close proximity to each other.

As for the heart-signals at the precordial electrodes, such as electrode 82 and electrode 84, the transmitters are as shown in connection with the limb signal transmitters just described. Again, the frequencies are set differently, each from the other, but at higher frequencies; this is not a problem. Also, because the field strength of the signals from the various electrodes associated with transmitters is low, there is considerable freedom in choosing a frequency which is free of local interference. There are generally six precordial electrodes, and, therefore, in this system there are six precordial channels (for simplicity, only the first and sixth are shown in FIG. 1; however, each channel not shown is similar to those shown), each having the transmitting and receiving structures of corresponding elements in the limb signal channels. For example, the signal from the first precordial electrode 82 and its associated transmitter is received by antenna 86 and is fed to receiver-demodulator 88 where a signal in the audible or sub-audible frequency range is obtained and fed to decoder 90 for any decoding that is necessary to reproduce the heart-signal. The heart-signal thus derived is applied to buffer amplifier bank 92. Similarly, the heart-signal detected at the sixth precordial electrode 84 is transmitted by the associated transmitter and is received by antenna 94, following which it is detected and demodulated by receiver-demodulator 96, and, if necessary, it is then decoded by decoder 98 and fed to buffer amplifier 92. Buffer amplifier 92 is a bank of amplifiers, one for each of the six precordial signal channels. The limb signals and the precordial signals are fed, without loss of integrity, to lead selector 100 which is of the conventional type found in commercially available electrocardiographs and which permit selection of each of the channels individually. The output signals of lead selector 100 are fed to filter-amplifier 102, following which the signals are fed to the electrocardiographic analog or digital cardiographic display. The analog recording pens are represented by needle 104. The galvanometric mechanism is represented by element 106. Alternately, selected ones of the signals shown entering lead selector 100 may be fed directly to a monitor 107 or to a Holter system 109 for developing a twelve-lead electrocardiogram from the signals sensed by the electrodes placed only on the chest area.

Figure 2:
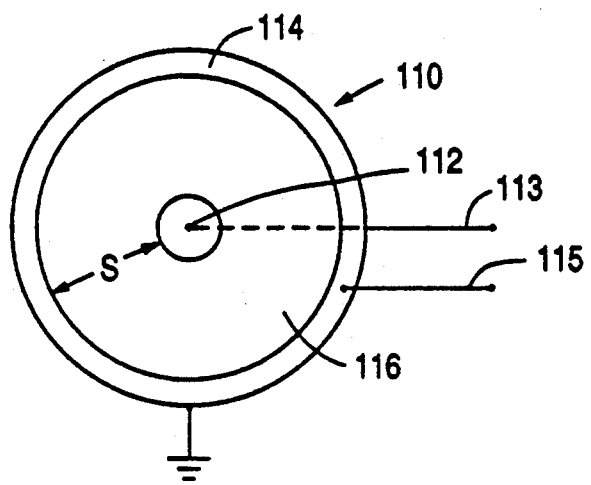
FIG. 2 is a schematic diagram of a concentric dipole electrode for use in the present invention.

Turning to FIG. 2, there is shown one dipole electrode patch configuration for use with the present invention.

Electrode patch 110 includes signal contact element 112 that is electrically conductive in nature and has a conductor 113 associated therewith for coupling, for example, to the microchip amplifier, the encoder-modulator, the transmitter element of FIG. 1, or to external equipment. Contact 112 may be made of aluminum, for example. Contact 114 is the indifferent or reference contact with the spacing "S" between contact 114 and contact 112 being typically 2-4 cm. Of course, concentric ring contact 114 is electrically conductive in nature. In some cases it may not be a closed circle but may merely be an arc of a circle. Contacts 112 and 114 are carried on an electrically non-conductive plastic film body 116, for example. If contacts 114 and 112 are too widely separated, the accuracy of the graphic reproduction of the heart-signal will be diminished.

Figure 3:
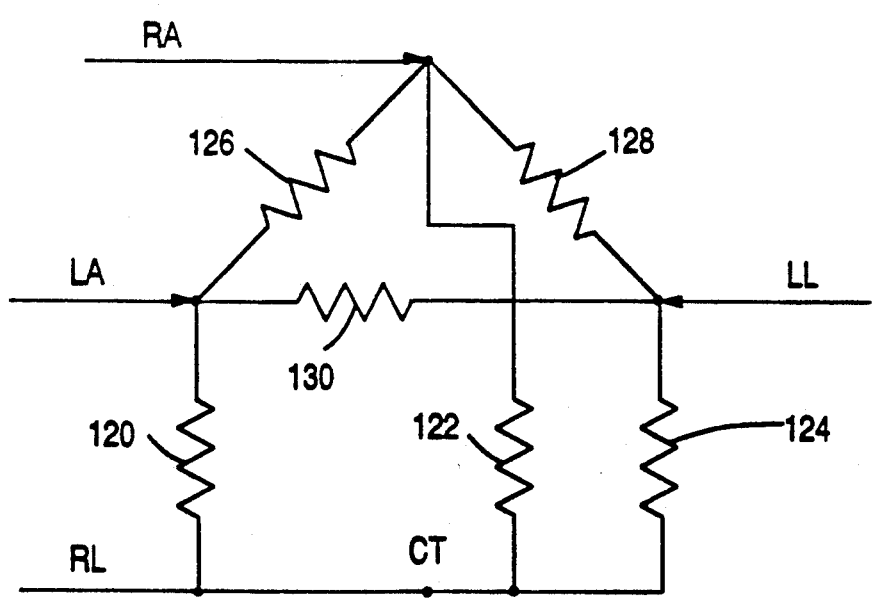
FIG. 3 is a schematic diagram of a "Wilson" network or bridge for developing an indifferent signal.

In FIG. 3 the so-called "Wilson" network is shown. The purpose of this network is to establish a zero area of the field from the heart dipole which is creating the field being studied. As can be seen from FIG. 3, the right arm, left arm, and left leg potentials are combined through three equal resistors 120, 122, and 124 to establish a zero or reference point which is generally referred to as the central terminal. The size of each of resistors 120, 122, and 124 is in excess of 5,000 ohms with the general range being 5,000-15,000 ohms. The CT potential is not actually zero. Theoretically, the potential of the CT is the mid-dipole potential of the heart-signal generator if the field is homogenous and if the dipole generating the signal lies exactly in the center of an equilateral triangle, the angles of which are formed by the three electrode points LA, RA and LL. Resistors 126, 128 and 130 have the same resistance and form an electrical equilateral triangle simulating the Einthoven triangle of the electrocardiographic art.

Figure 4:
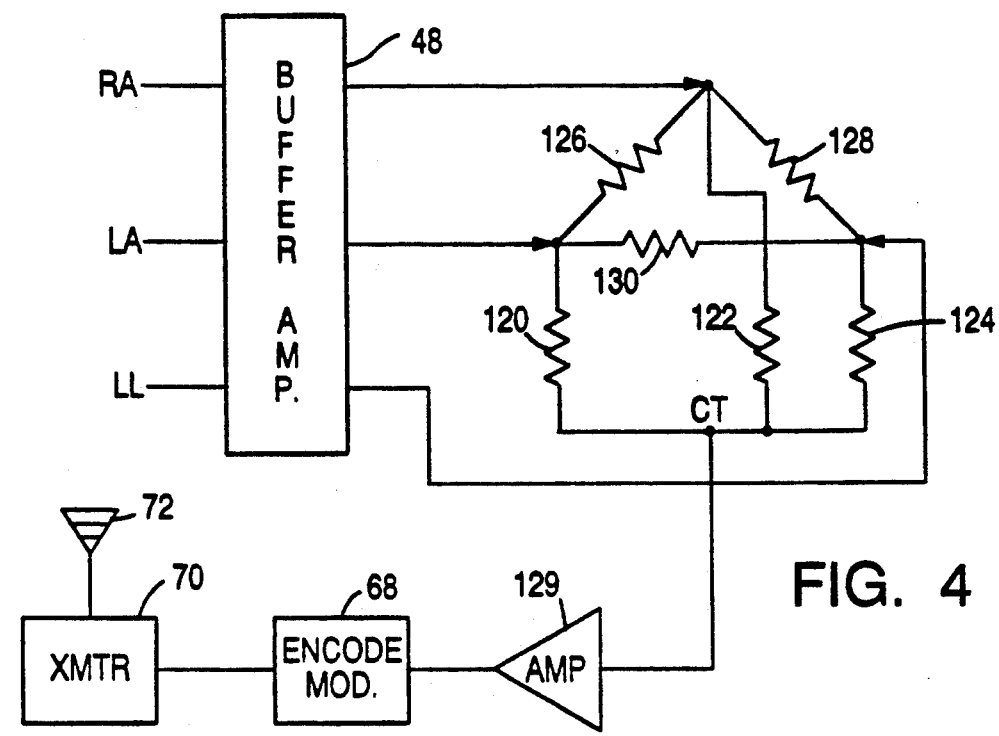
FIG. 4 is a schematic diagram of an alternative circuit for developing a right leg signal.

According to the embodiment of FIG. 4, the CT potential, after amplification by amplifier 129, is transmitted by transmitter 70 through antenna 72 to receiver-demodulator 76 and its associated components for application to the right leg electrode 14, shown in FIG. 1.

Unipolar leads are presently the only ones used in the precordial positions, such as in FIG. 1A. It was formerly believed that a limb could serve as the indifferent or reference connection because it was relatively so distant from the precordial electrode. It soon became apparent, however, that this was not the case, that the arm or leg was not truly indifferent, and that it altered the results in varying degrees depending upon which limb was connected to the negative terminal of the electrocardiograph. Thus, there was a need to establish a central terminal, as described hereinbefore.

Associated with each of the limb and precordial electrodes is a power supply 111 (conventionally a battery) which provides to the microchips operating voltage of the necessary polarity and magnitude. At the base station side, integrated circuit (IC) operating voltage of the necessary polarity and magnitude is provided by power supply 115 which may be battery or AC based.

From FIGS. 5, 12A, and 12B, it is apparent that each electrode patch 110 carries its own power supply 150 as well as the necessary Microchips 152, which are powered by power supply 150, and an antenna 154. An LED 21 may also be provided which lights with each heart beat. Tab 161 is an insulating member which, when pulled, connects power supply 150 to the microchips and activates the associated electrode assembly. This is true for the receiving electrode 14 on the right leg as well as for the various transmitting electrodes.

FIGS. 12A and 12B are perspective views of a typical electrode assembly of the present invention. They each show an electrode assembly housing 153 mounted on an electrode 110. On top of housing 153 there is shown an electrode position indicator 155; in these views the letters "PA" designate that this electrode assembly is for use on the right arm of the patient. Other means for identifying the electrode assemblies can be used, such as color coding. No matter what form of coding is used, each of those codes needs to be designed to minimize the possibility of error caused by installation of the electrodes in the wrong location on the patient.

Also shown in these figures is a frequency change switch 176 which could be a detented wheel type switch so that each frequency position is well defined and the operator will easily know which setting the frequency is in. Similarly, there is an encoding selector switch in either a detented wheel switch configuration shown as switch 175, or a DIP switch 174.

FIG. 12A is also partially cut away to show the printed circuit board 156 that is internal to the assembly with a battery 150 mounted to board 156 and making contact thereto via battery clip 151. Serially connected to battery clip 151 is a pair of electrically conductive spring fingers 159 which are mounted adjacent each other. Between fingers 159 is tab 161 which prevents contact of fingers 159 with each other. The combination of tab 161 and fingers 159 therefore act as an on/off switch which prevents battery 150 from discharging prior to use and allows the operator to very positively activate the electrode assembly by completely removing tab 161. If such an assembly is to be reused, tab 161 should be reinserted between fingers 159 to deactivate the circuitry.

Figure 6:
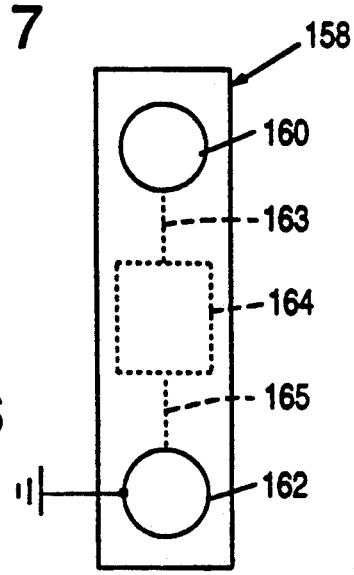
FIG. 6 is an elevational view of an alternative form of a dipole electrode structure.

FIG. 6 shows an alternative form of a dipole electrode structure 158 which is particularly useful for precordial application. The necessary separation of signal electrode 160 and zero reference electrode 162 is achieved in the limited space available on the chest. This strip electrode structure carries a microchip amplifier, an encoder-modulator, and a transmitter module 164 (with battery) and connectors 163, 165 for signal input.

Each dipole electrode structure 158 may have a multiple-position switch which changes the frequency or digital encoding of the signal from the electrode so that it matches the parameter for the site at which it is to be used on the patient in order to limit the number of electrodes with different operating parameters which must be kept in inventory and employed in setting up the system for a given patient.

The electrodes may be color coded or labeled to indicate where they should be placed on the body. They may also include frequency or code switches to permit one electrode type to be usable in various body locations.

Figure 11:
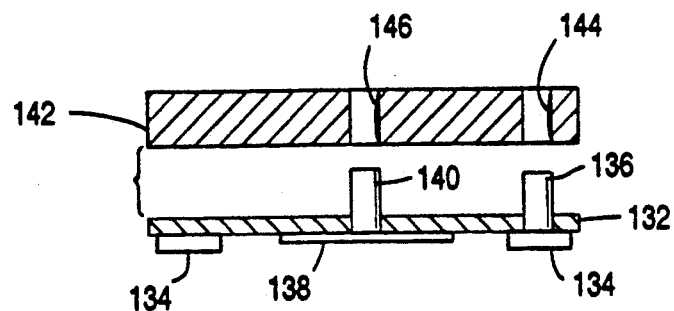
FIG. 11 is a cross-sectional side view of a snap mounting configuration for removably mounting a transmitter assembly to a disposable electrode.

FIG. 11 illustrates another form of electrode/electronics assembly that may be of interest in some applications. This assembly consists of two portions, an electrode assembly 132 that may be disposable, and an electronics assembly 142 that may be reusable. Electrode assembly 132 includes reference contact 134 and its associated connection position post that extends through the insulative body of the electrode to the side opposite the contact, and signal contact 138 and its connection post 140 that also extends through the body of the electrode. Electronics assembly 142 is sized and configured to mount onto electrode assembly 132 and to mate with connection posts 136 and 140 which are disposed to be received by contacts 144 and 146, respectively.

Each of the contacts 144 and 146 are spring loaded to make electrical contact with and to physically capture connection posts 136 and 140.

Figure 7:
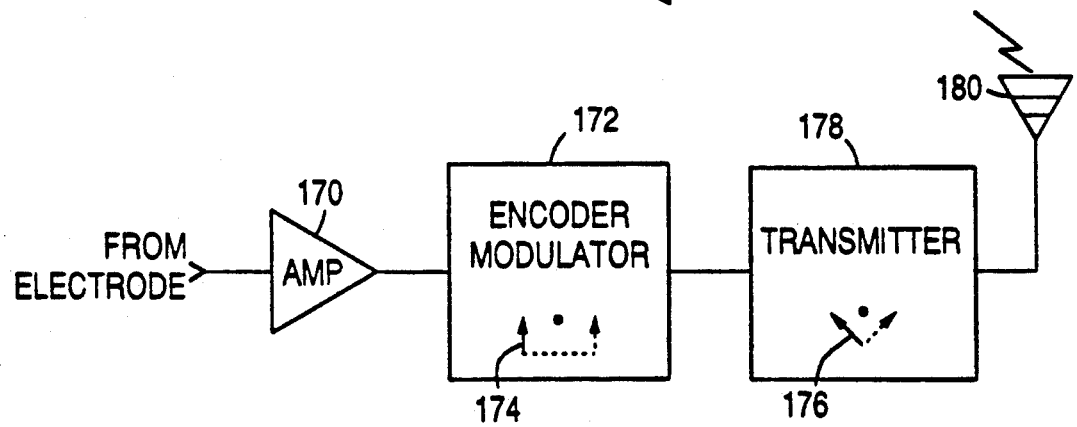
FIG. 7 is a block diagram of an electrode transmitter means with provision to switch the enabler code and the transmitter frequency.

FIG. 7 illustrates in block form this capability. In FIG. 7, heart-signals from any of the ten electrodes are coupled to amplifier 170, as shown in FIG. 1. The output of amplifier 170 is fed to encoder-modulator 172 which includes a quad NAND gate section as is found, for example, in a type TSC-323 integrated circuit. DIP switch 174 permits selection of a three-digit code if digital encoding is used. On the other hand, if analog encoding is to be used, a frequency-change switch 176 is provided on transmitter 178. The oscillators described in connection with FIG. 1 (which are used here) are tunable by changing the applied voltage. Such voltage change is accomplished by using switch 176 to vary the voltage applied to the control line of a voltage controlled oscillator (VCO) that is a portion of the transmitter. Thus, by either method, the number of different types of electrodes that must be inventoried can be reduced. The base station decoders or receiver-demodulator may be fixed, and the electrode encoding means may be adjusted to correspond to the code or frequency of a target signal channel at the base station. A similarly equipped receiver-demodulator would also have to be provided to make similar adjustments either to the decoder or to the center frequency of the receiver.

The appropriately encoded signal, or the signal at the desired frequency, is fed to antenna 180.

This system is adapted to work with Holter systems in which twelve-lead electrocardiograms are derived from three-electrode information. This fact is illustrated by element 109 in FIG. 1.

The unipolar leads with respect to the right arm, left arm and left leg of the patient are traditionally measured with respect to the right leg as the reference point. With a system wherein each signal is individually transmitted to a base station, it is undesirable to run a wire from the right arm, left arm and left leg electrodes to the electrode attached to the right leg of the patient as a reference point. In the embodiment disclosed in FIG. 1, the reference point of the right leg is created from the signals at the other extremities of the patient in the base station and then transmitted to the right leg electrode, as discussed above. This is the ten-electrode assembly approach. The right leg has historically been used as the reference point substantially because the earlier instrumentation lacked the sensitivity and the noise rejection capabilities of today's electronic devices.

After additional experimentation it has been determined that a reference point that is closer to the signal electrode than the right leg can be used, and that each of the three signals necessary to determine the bipolar leads I, II and III, as well as the unipolar leads aVR, aVL and aVF and $V_1$ through $V_6$, can be measured with respect to different reference points without reconstructing a common reference point signal. Today's electronics requires that each of these reference points be at least 2-4 cm. from the corresponding signal contact. Electrodes such as those shown in FIGS. 2 and 6 could be used for this purpose, for viewing the shape of the electrocardiograph signals and their amplitude. The controlling factor is therefore the ability of the electronics to extract the needed signals from the background noise. This is practiced in the nine-electrode assembly approach.

Figure 8:
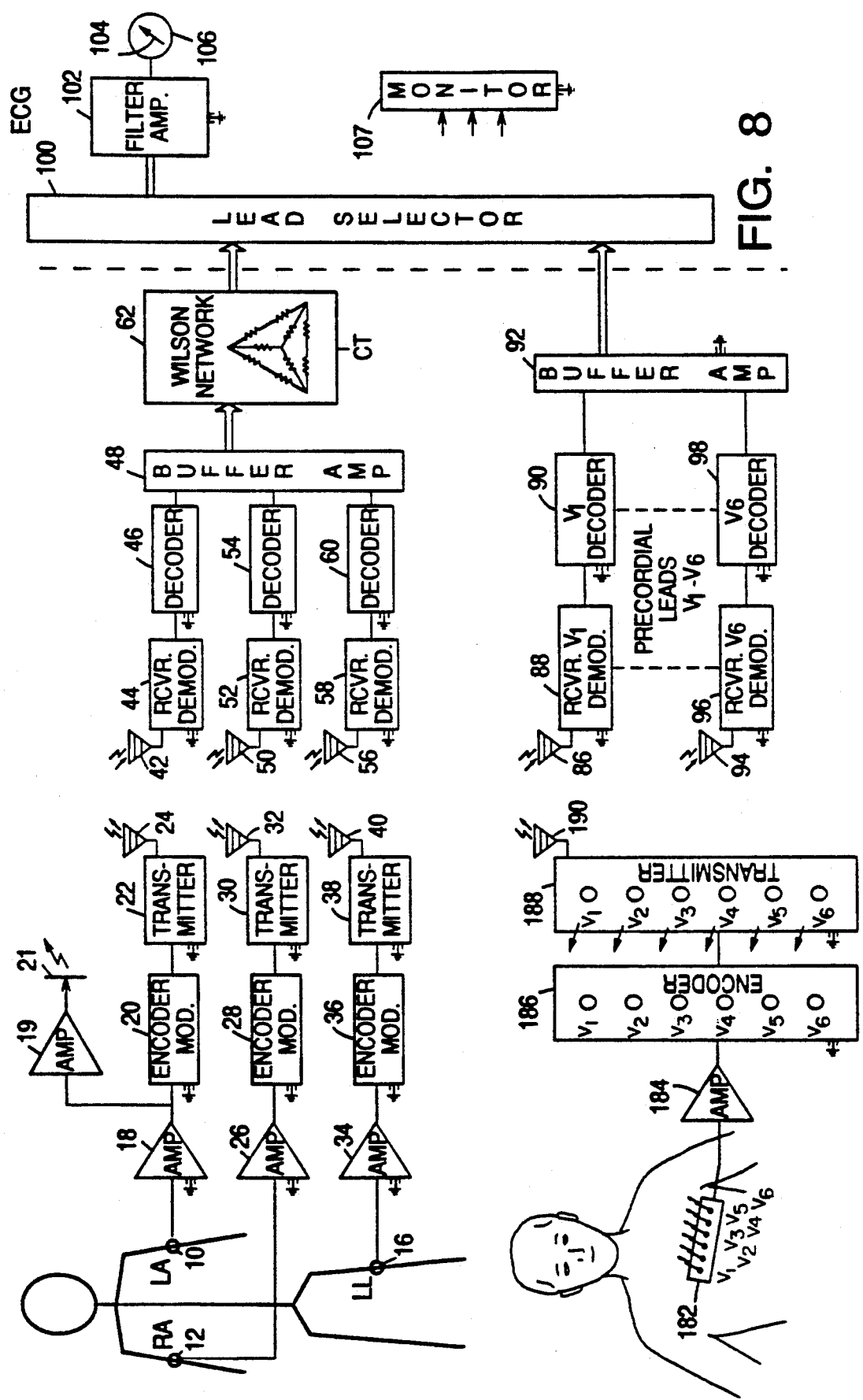
FIG. 8 is a block diagram of a wireless electrocardiograph system according to a second embodiment of the present invention.

Therefore, a second embodiment of the present invention is a system as shown in FIG. 8 which does not have the receiving and transmitting paths associated with the reference electrode positioned on the right leg of the patient, as shown in FIG. 1.

Figure 10A:
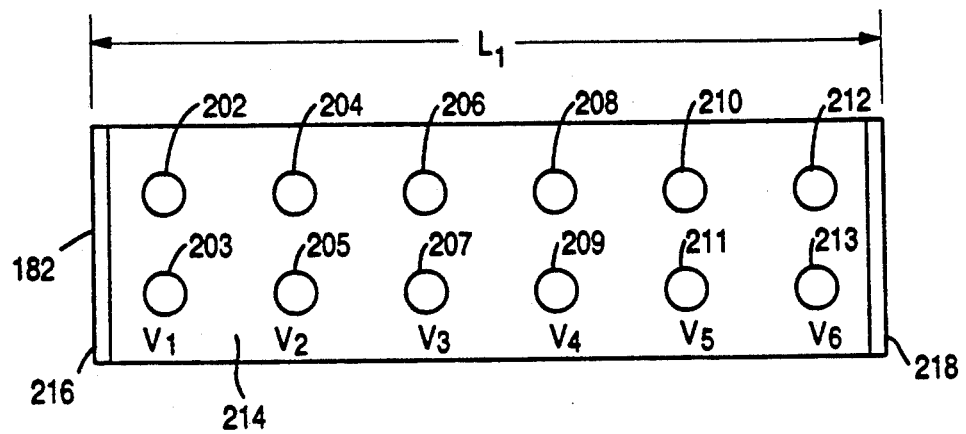
FIG. 10A is a plan view of the electrical contact side of an electrode strip of one configuration for the six precordial electrodes for easy mounting on the chest of the patient.

In a continuing effort to make the wireless ECG system of the present invention even more foolproof, a precordial dipole electrode strip 182 has been designed. (See FIGS. 8 and 10A.) Strip 182 includes a pair of contacts 202-213 (signal contacts are even numbered, and reference contacts are odd numbered) for each precordial signal measurement. Each of the contacts 202-213 is mounted or aligned on one side of strip 182 in a line or row in a spaced-apart relationship to the other contact mounted or aligned on the other side of strip 182 in another line or row, and each of the contacts 202-213 has a connecting post, or the like, that extends through strip 182 to the opposite side. Precordial transmitter assemblies are mounted to the other side of strip 182 and electrically connected to the appropriate connecting post. The precordial electrodes are to be located on the body of the patient, evenly spaced, with the first being approximately 1 cm. to the left of the patient's sternum, and the sixth approaching the patient's side. To accomplish this, various lengths of precordial electrode strips 182 could be manufactured. Alternatively, the base material of strip 182 could be elastic, similar to an elastic bandage. To hold strip 182 to the chest of the patient, adhesive areas 216 and 218 can be provided at either end of strip 182. Alternately, the entire contact side 214 of strip 182 can be coated with an adhesive other than on the faces of the twelve contacts. This is the four-electrode assembly approach.

Figure 9:
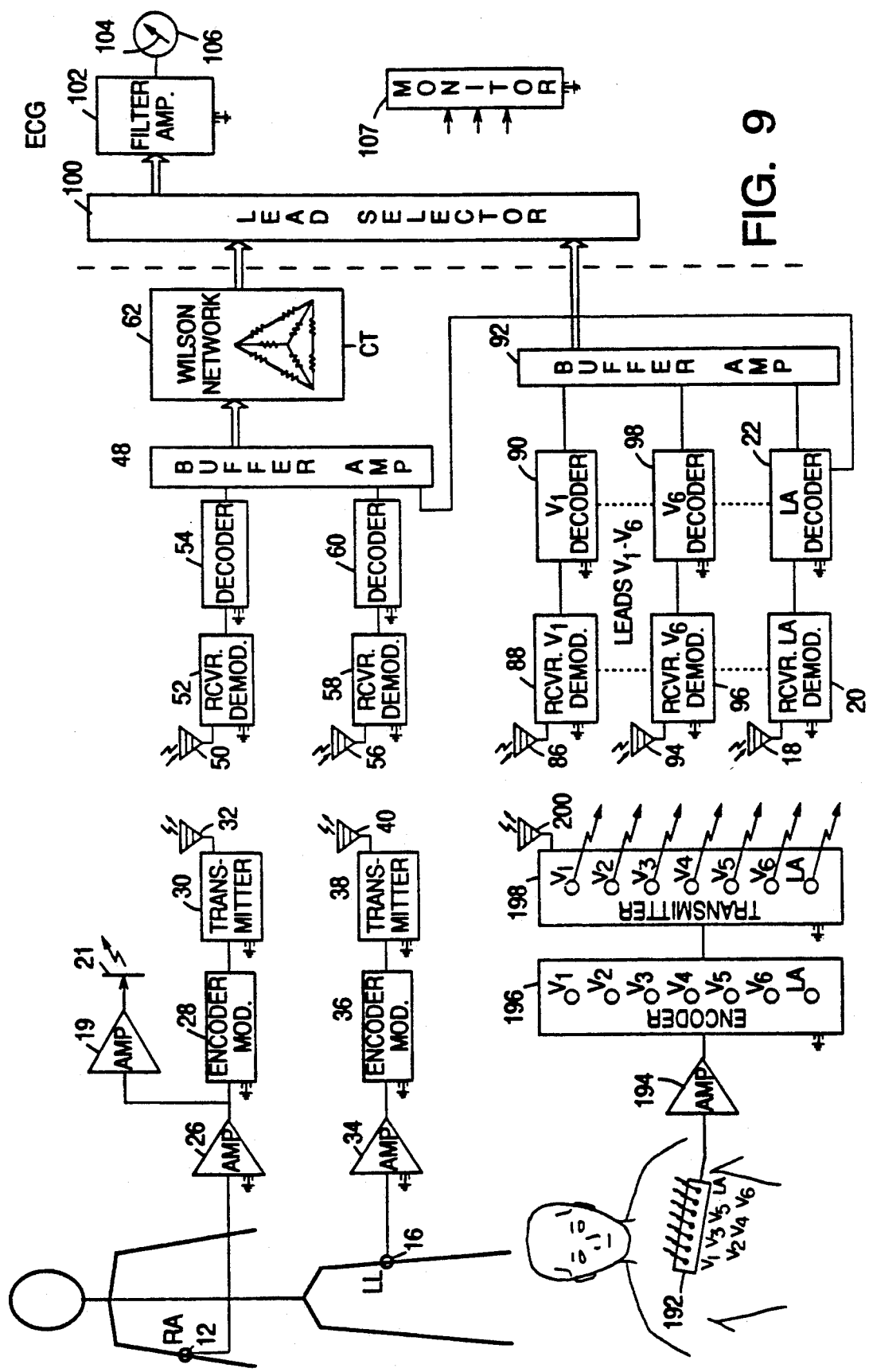
FIG. 9 is a block diagram of a wireless electrocardiograph system according to a third embodiment of the present invention.
Figure 10B:
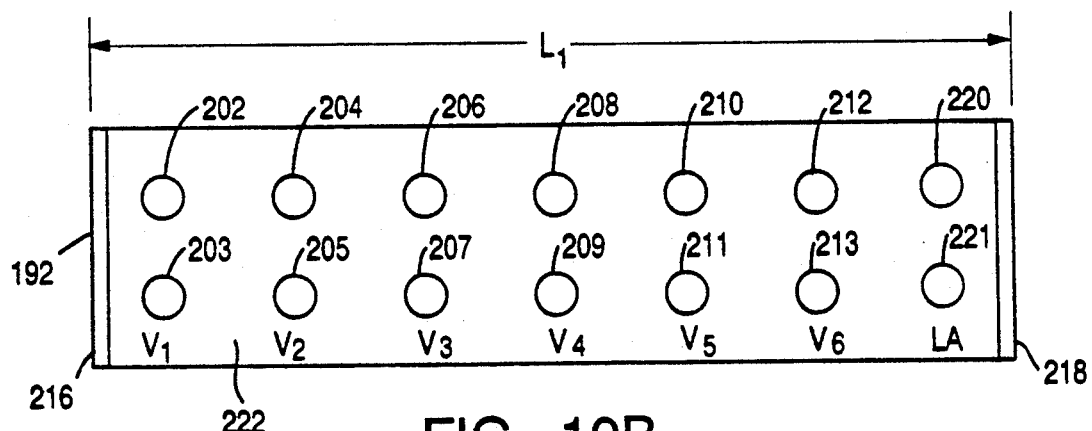
FIG. 10B is a plan view of the electrical contact side of an electrode strip of a second configuration for the six precordial electrodes and the left side electrode for easy mounting on the chest of the patient.

Additional experimentation has shown that the left arm dipole electrode can be moved to the left side of the patient with no loss in accuracy of the resulting ECG data. As a result of this experimentation another embodiment of the present invention is the lengthening of the precordial dipole electrode chest strip of FIG. 10A to include a pair of contacts 220 and 221 to monitor the left arm signal at the left side of the patient. The extended strip 192 is shown in FIG. 10B, and the corresponding electronics is shown in FIG. 9. This is the three-electrode assembly approach.

In either of the embodiments of FIGS. 8 and 9 the transmitting assemblies attached to strip 182 or strip 192 may be individual units that are attached to the appropriate connection posts of the various electrodes, or they may be individual transmitters which are all contained within a common housing. The transmitting assemblies in FIGS. 8 and 9 include encoders and transmitters 186 and 188 or 196 and 198, respectively.

Reference to only a wireless ECG has been made up to this point in this Specification. However, the wireless transmission of signals from a patient, regardless of the function being monitored, can be transmitted and received remotely in the same way. Thus, a truly wireless monitoring system that includes pulse, temperature, etc. can be easily accomplished with the transmitting and receiving devices of the present invention.

Figure 13:
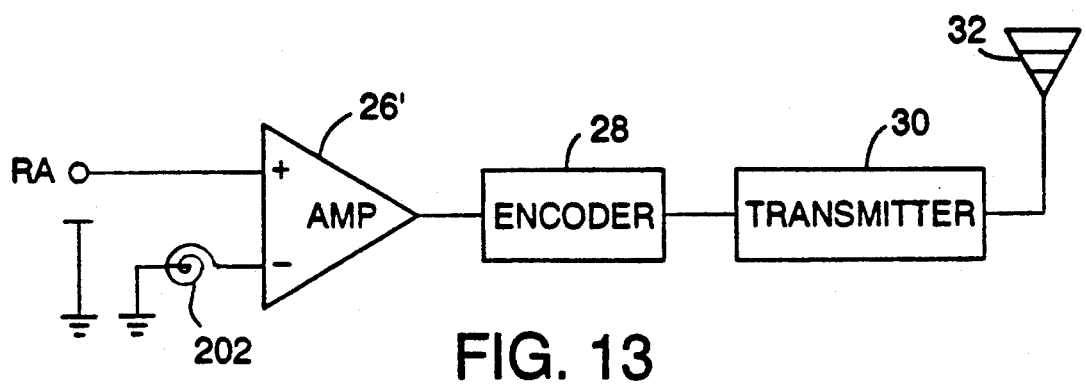
FIG. 13 is a block diagram of circuitry used in the apparatus.

To further improve the possibility of the dipole electrode assemblies to separate the desired signal from the background noise, amplifiers such as 26 and 34 can be differential input amplifiers as shown in FIG. 13. Differential input amplifier 26' includes two signal input terminals—an inverting terminal and a non-inverting terminal. The signal from the right arm dipole electrode is connected to the non-inverting terminal, and a noise pick-up coil 202 is connected to the inverting terminal. The purpose of noise pick-up coil 202 is to detect the background noise and to apply that to amplifier 26'. The theory is to subtract or reduce the background noise from the signal that is included with the signal from the right arm dipole electrode. This is accomplished by the difference in sign of the two input terminals of amplifier 26' since the output signal from amplifier 26' is the arithmetic difference between the two input signals that have been amplified by a selected factor. Thus, including this type of amplifier in each of the transmitter assemblies will largely reduce the signal noise and permit the use of less sensitive components or will allow the use of dipole electrode patches that have a smaller spacing between their signal and reference contacts.

FIG. 14 is another embodiment of dipole electrode structure 158 illustrated in FIG. 6 which includes a detachable microchip 230 to permit reuse thereof. Structure 158 includes a non-conductive layer of plastic material 231 with signal electrode 160, reference electrode 162 and a chip receptacle 232 mounted thereon. Structure 158 further includes connectors 163 and 165 which electrically connect and couple electrodes 160 and 162 to chip receptacle 232. Chip receptacle 232 is provided with a plurality of sockets 233, four of which are represented in FIG. 15.

Microchip 230 has electronic components substantially similar to those contained in microchip 164, including an amplifier, an encoder-modulator and a transmitter, and can be snapped on and off of structure 158. To facilitate its attachment and removal from structure 158, microchip 230 has a plurality of prongs or pins 234, four of which are represented in FIG. 16. Prongs 234 cooperatively mate with sockets 233, as shown in FIG. 14, when -microchip 230 is attached to chip receptacle 232.

A further embodiment of the invention which permits transmission of a multichannel twelve-lead electrocardiogram on a digitally encoded radio frequency signal by means of a single frequency channel is illustrated in the drawings starting with FIG. 17. Precordial strip assembly 321 of the present invention is for use on a patient 322 having a body 323 with a heart 324 and a precordium or precordium area 326 overlying heart 324. Body 323 is covered by an outer layer of skin 327. Patient 322 also has right and left arms 328 and 331 and right and left legs 332 and 333. Strip assembly 321 includes an elongate strip or strip means 336 generally horizontal "S" shaped in conformation.

Figure 18:
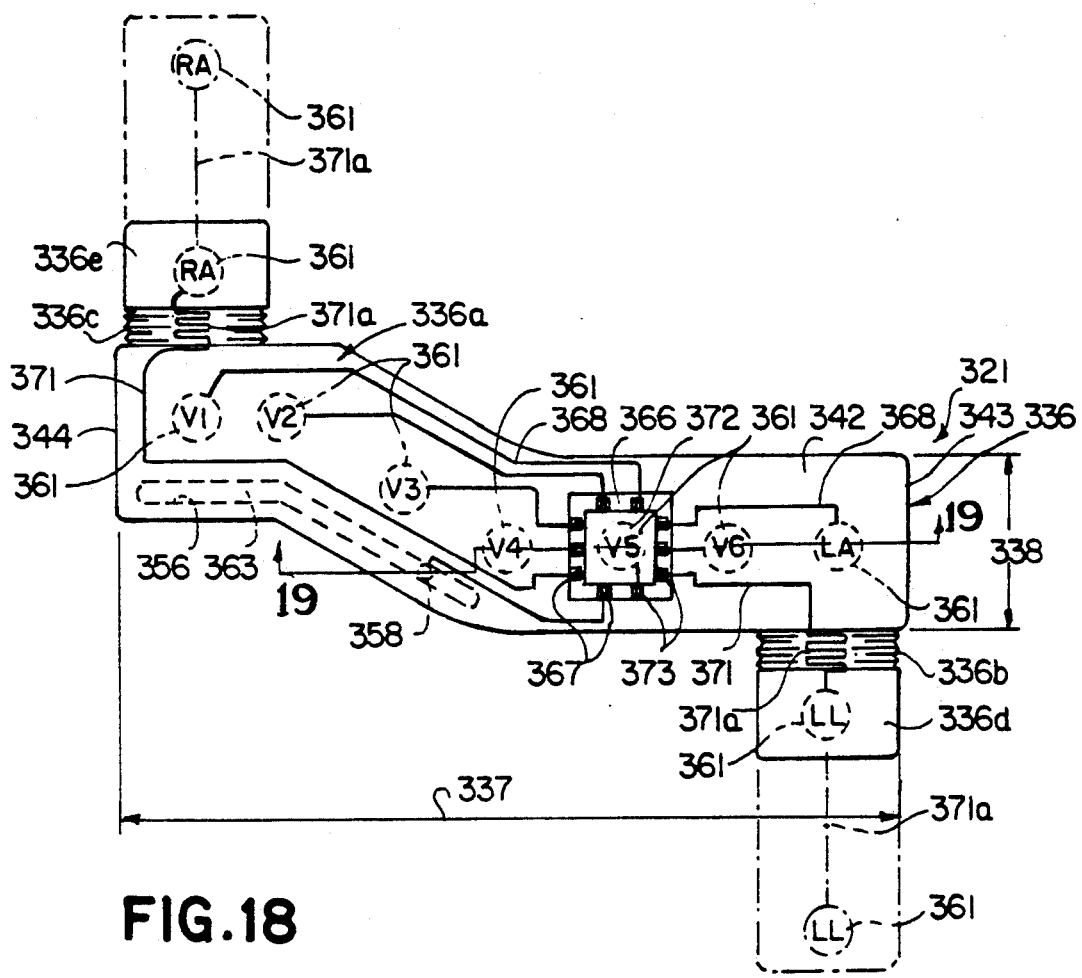
FIG. 18 is a top plan view of the precordial strip assembly shown in FIG. 17.
Figure 19:
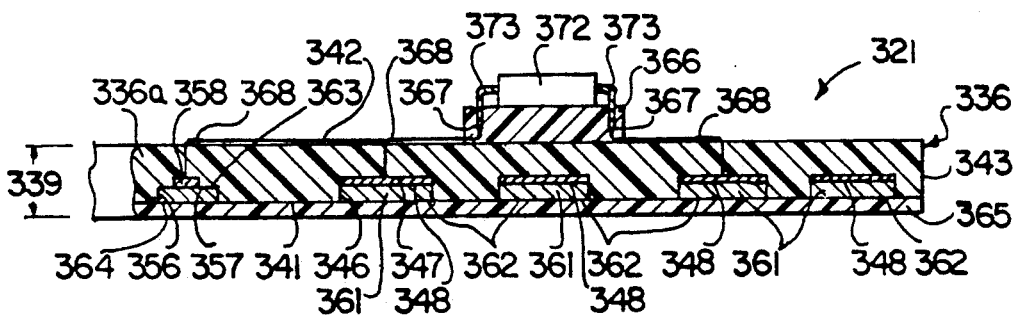
FIG. 19 is a cross-sectional view of the precordial strip assembly shown in FIG. 18 taken along the line 19—19 in FIG. 18.

Strip 336 has a length and a width identified by dimensions 337 and 338 in FIG. 18 and a height identified by dimension 339 in FIG. 19. Length 337 can range from five to thirty-eight centimeters, width 338 from two to five centimeters, and height 339 from one-third to one and one-half centimeters. Strip 336 can be made in various sizes to fit the desired range of pediatric, male or female patients.

Strip 336 is comprised of a central elongate portion 336a which is generally linear and has first or left and second or right ends 343 and 344. Strip 336 has first and second elastic portions 336b and 336c which commence near first and second ends 343 and 344, respectively, and first and second extendable or stretchable portions 336d and 336e adjacent elastic portions 336b and 336c. Elastic portions 336b and 336c protrude from central portion 336a at approximately right angles, and extendable portions 336d and 336e are substantially colinear with elastic portions 336b and 336c, respectively. Strip 336 further has first and second surfaces 341 and 342.

Strip 336 can be made from a suitable non-conductive, insulating and flexible plastic sheet formed from a layer of material such as polyurethane or polyvinyl chloride (PVC), or a combination thereof. Polyurethane offers flexibility with relative stiffness. Its hardness (e.g., Shore A 21, 41, 81 or 90) can be adjusted by blending materials of various hardness to obtain the desired flexibility and stiffness. Thus, if desired, the hardness of strip 336 can be varied from one portion to another to provide elastic portions 336b and 336c which are stretchable to permit pulling of extendable portions 336d and 336e from positions near central portion 336a to positions remote central portion 336a. Polyvinyl chloride offers higher flexibility by using variations in the thickness of the material. Thus, single or multiple layers can be provided with the same thicknesses or tapered thicknesses.

Strip 336 is provided with a plurality of spaced apart cylindrical receptacle bores 346 commencing in first surface 341 and terminating at inner surface 347 of strip 336, one of which is identified in each of FIGS. 18 and 19. A thin cylindrical conductive pad 348 is disposed in each receptacle bore 346 and mounted to inner surface 347. Central portion 336a of strip 336 is also provided with an elongate recess 356 terminating at inner surface 357 of strip 336. A conductive pad 358 is embedded in a portion of inner surface 357 as shown in FIG. 19.

A plurality of conductive contact elements or conductive elements 361 are mounted in spaced apart positions along the length of strip 336 for detecting heart signals from patient 322. Conductive elements 361 are generally cylindrical in conformation and have a contact surface 362 and dimensions which permit their disposition in receptacle bores 346 such that contact surface 362 is exposed on and generally in the plane formed by first surface 341 of strip 336. Conductive elements 361 are fastened to conductive pads 348 with a suitable conductive adhesive.

Conductive elements 361 include six precordial elements identified as $V_1$ through $V_6$ mounted sequentially across first surface 341 of central portion 336a with the $V_1$ conductive element adjacent second end 344 of central portion 336a. Conductive elements 361 also include a seventh conductive element 361 identified as LA mounted on first surface 341 of central portion 336a adjacent first or left end 343 and the $V_6$ conductive contact element (at the very left side of central portion 336a of strip 336, at midaxillary line position, as viewed by patient 322). Two additional conductive elements 361 identified as LL and RA are mounted in first and second extendable portions 336d and 336e, respectively. Conductive element LL on extendable portion 336d is separated or set apart from adjacent conductive element LA on central portion 336a by first elastic portion 336b, while conductive element RA on second extendable portion 336e is separated or set apart from adjacent conductive element $V_1$ on central portion 336a by second elastic portion 336c.

First and second elastic portions 336b and 336c serve as stretchable means. First elastic portion 336b permits spacing of LL conductive element 361 between a first position in close proximity with $V_1$ through $V_6$ conductive elements 361 and adjacent LA conductive element 361 and a second position or "floating" position remote therefrom as illustrated in FIG. 18. Second elastic portion 336c permits spacing of RA conductive element 361 between a first position in close proximity with $V_1$ through $V_6$ conductive elements 361 and adjacent conductive element $V_1$ and a second position or "floating" position remote therefrom also illustrated in FIG. 18. First and second elastic portions 336b and 336c stretch and extend approximately five to fifteen centimeters to permit spacing of LL and RA conductive elements 361 in a second remote position. Elastic portions 336b and 336c of strip 336 contain suitable elastic qualities, such as those discussed above, to urge LL and RA conductive elements 361 towards their first position.

An elongate reference contact element or reference element 363 having a contact surface 364 and made of a suitable material such as copper or a silver derivative is carried by central portion 336a of strip 336 and serves as a common reference for conductive elements 361. Reference element 363 is mounted in elongate recess 356 such that contact surface 364 is exposed on and generally in the plane formed by first surface 341 of central portion 336a. Reference element 363 is fastened to inner surface 357 in a suitable manner and to conductive pad 358 with a suitable conductive adhesive. It should be appreciated by those skilled in the art that reference element 363 is within the scope of the present invention if it is a single long element, is partially extended and/or consists of several electrically connected segments, regardless of whether the segments are adjoining. In addition, reference element 363 may have a circular, ring shaped or other conformation and/or be located elsewhere on strip 336.

Most desirably, first surface 341 of at least central portion 336a and first and second extendable portions 336d and 336e of strip 336 is adhesive to permit retention of contact elements 361 and 363 and strip 336 in proper position when strip assembly 321 is placed on precordium area 326. Adhesive first surface 341 carries a protective covering 365, as illustrated in FIG. 19 with respect to central portion 336a, which is removed therefrom to expose first surface 341 for placement on precordium area 326. Protective covering 365 may be of a one piece or segmented design; a one piece design would permit removal of the protective covering in a single removal action. It should be appreciated by those skilled in the art that first surface 341 may have adhesive characteristics only in the vicinity of contact elements 361 and 363, or contact elements 361 and 363 may be retained in position on the patient by other means, and be within the scope of the present invention.

Chip receptacle 366 serves as junction means carried in a single region by central portion 336a of strip 336, as illustrated in FIGS. 18 and 19, and has a sufficient number of pin sockets 367 for receiving the heart signals detected by contact elements 361 and 363. Chip receptacle 366 is mounted on second surface 342 of central portion 336a by a suitable adhesive.

Conductive pad 358 and each cylindrical conductive pad 348 on central portion 336a is connected by a thin conductive wire 368 to a pin socket 367, with wires 368 and conductive pad 358 or cylindrical conductive pads 348 serving as means for electrically coupling and connecting reference element 363 and $V_1$ through $V_6$ and LA conductive elements 361, respectively, to chip receptacle 366. (Several representative pin sockets 367 and wires 368 are identified in FIGS. 18 and 19.) Wires 371 and cylindrical conductive pads 348 on extendable portions 336d and 336e serve as the means for electrically coupling and connecting LL and RA conductive elements 361 to chip receptacle 366, and have extendable or stretchable portions 371a which are urged towards a first position when extendable portions 336d and 336e are in a first position and capable of extension to a second position when extendable portions 336d and 336e are in a second remote position. By electrically coupling and connecting conductive pads 348 and 358 to chip receptacle 366, wires 368 and 371 serve to electrically couple and connect conductive elements 361 to reference element 363.

A microchip 372 is mounted on second surface 342 of central portion 336a of strip 336 in contact with the junction means for transmitting a radio frequency signal which carries the heart signals detected by contact elements 361 and 363. More specifically, microchip 372 receives the heart signals detected by precordial $V_1$ through $V_6$ conductive elements 361, LA, RA and LL conductive elements 361, and reference element 363 (See FIG. 20). Microchip 372 is received by chip receptacle 366 for retention on strip 336 and has a plurality of pins 373 which cooperatively mate with pin sockets 367 (See FIG. 19). Microchip 372 may be detachably mounted to chip receptacle 366. For example, microchip 372 can be plugged into and ejected out of chip receptacle 366 mounted on strip 336 of strip assembly 321.

Microchip 372 includes means for transmitting a single encoded radio frequency signal which carries the twelve-lead electrocardiographic multiple heart signals detected by contact elements 361 and 363, and comprises one or more microchip amplifiers and filters, a multiplexer, a microchip encoder-modulator, a microchip transmitter, a wireless-signal radiator and a battery means. Microchip 372 can transmit a time multiplexed and modulated multichannel twelve-lead electrocardiogram by a digitally encoded radio frequency signal via a single frequency channel.

Some of the components of the wireless electrocardiograph monitoring system contained in microchip 372 are illustrated in FIG. 17. Microchip 372 includes amplifiers 381 (shown for simplicity as a single amplifier), encoder-modulator 382 (which includes an analog-to-digital converter and a multiplexer), transmitter 383 and wireless-signal radiator or sending antenna 386. The digitally encoded radio frequency signal containing the time multiplexed and modulated multichannel twelve-lead electrocardiogram is received by receiving antenna 387, after which it passes through receiver-demodulator 388, decoder 391, buffer amplifier 392, electrocardiograph lead selector 393 and filter amplifiers 396 (shown for simplicity as a single amplifier). From filter amplifiers 396, the twelve signals detected by the twelve-lead electrocardiogram can be sent to an electrocardiographic printer 397, a monitor 398 and/or a Holter recording 399.

Figures 20, 21:
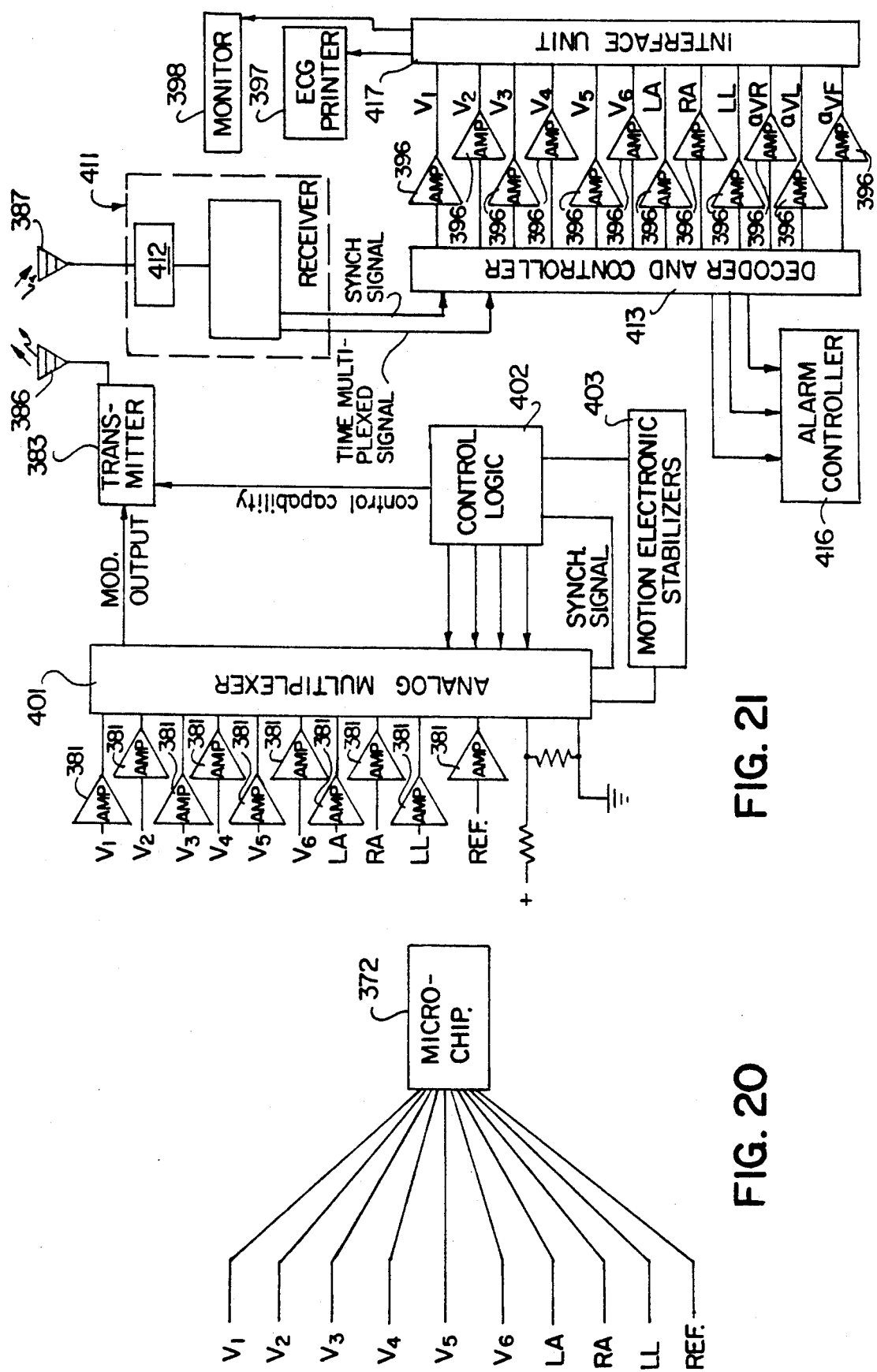
FIG. 20 is a diagram of a portion of the wireless electrocardiograph system shown in FIG. 17.
FIG. 21 is a more detailed block diagram of the wireless electrocardiograph system shown in FIG. 17.

A more detailed diagram of a wireless electrocardiograph monitoring system is illustrated in FIG. 21. Microchip 372 has a separate amplifier for amplifying to a more workable level the relatively weak heart signals detected by $V_1$ through $V_6$, LA, RA and LL conductive elements 361 and reference element 363. Each amplifier 381 can include a filter for removing or suppressing undesirable portions of the detected signal; this filter may be similar to that contained in differential input amplifier 26'. Each microchip amplifier with filter has a signal input terminal coupled to each pin 373 carrying a heart signal from a conductive element 361 or reference element 363, and an output terminal for sending the amplified and filtered heart signals.

The output of each amplifier 381 is connected to an input to analog multiplexer 401, a time-division multiplexed system, which combines the heart signals for transmission through a common channel. Multiplexer 401 includes an analog-to-digital converter for converting the analog heart signals detected by contact elements 361 and 363 to digital signals, and an encoder-modulator which changes the combined heart signals into an information signal suitable for propagation over a radio frequency. The encoder-modulator may include adjustment means for varying the digital encoding of the encoder-modulator.

Multiplexer 401 is connected to control logic 402 which monitors microchip 372 and the heart signals received thereby. A synchronized signal travels between multiplexer 401 and control logic 402 to permit monitoring of strip assembly 321. For instance, if patient 322 is out of range from the receiving unit or the battery powering microchip 372 is low, a warning may be triggered. Multiplexer 401 can also be connected to motion electronic stabilizers 403 (which in turn would be connected to control logic 402) for avoiding artifacts which can result in misleading readouts. (Artifacts create additional background noise which is picked up by contact elements 361 and 363 and reduces the accuracy of the electrocardiographic reading.) Multiplexer 401 has an output for transmission of a modulated output signal, and control logic 402 has an output for transmission of certain control capability information.

The outputs of multiplexer 401 and control logic 402 are connected to inputs to transmitter 383 which generates a high frequency electric current or carrier wave whose characteristics of amplitude, frequency or phase modulation are altered, or modulated, by the output signal from the encoder-modulator within multiplexer 401. Transmitter 383 may include an adjustment means for varying the frequency of operation thereof. The output of transmitter 383 is coupled to the input for the wireless-signal radiator 386 which radiates the signal over a single radio frequency.

Microchip 372 includes battery means, such as a 3 volt lithium coin cell, which serves as an exclusive power supply for strip assembly 321 and microchip 372 and has at least one voltage terminal for supplying power to microchip 372 and a ground terminal carried on first surface 341, possibly by reference element 363. Microchip 372 includes a means for applying operating potentials from the battery means to amplifiers 381, multiplexer 401, control logic 402, motion electronic stabilizers 403 and transmitter 383.

The radio frequency signal is received by antenna 387, which receives signals in quadrature configuration. The radio frequency signal is sent to receiver 411 which has a front end 412 and produces a synchronized output signal and a time multiplexed output signal. The outputs of receiver 411 are connected to the inputs of decoder and controller 413. Decoder and controller 413 is connected to alarm controller 416. The twelve electrocardiogram leads, detected and generated on patient 322 in accordance with both the unipolar and bipolar lead systems, are removed from the time multiplexed signal by decoder and controller 416 and separately fed through filter amplifiers 396 to interface unit 417. The twelve-lead electrocardiogram can be sent by interface unit 417 to an electrocardiographic printer 397 and/or a monitor 398.

It should also be appreciated by those skilled in the art that strip assembly 321 may have means for transmitting a time multiplexed and modulated multichannel twelve-lead electrocardiogram by a digitally encoded radio frequency signal via a single frequency channel which includes or consists of components other than those described above and/or accomplishes the transmitting of heart signals by means other than as discussed herein and still be within the scope of the present invention.

Strip assembly 321 is sized and configured such that $V_1$ through $V_6$ and the other conductive elements 361 are properly positioned on patient 322 to permit standard twelve-lead (I, II, III, aVR, aVL, aVF, $V_1$ through $V_6$) electrocardiographic monitoring. Contact elements 361 and 363 on strip 336 are adapted to contact skin 327 for detecting the required heart signals from patient 322 when strip assembly 321 is placed on precordium area 326 of patient 322. Placement of strip assembly 321 on patient 322 is relatively simple and quick. After selecting the proper size strip assembly to fit the size of the patient's thorax, protective covering 365 is removed from first surface 341 of central portion 336a of strip 336 to expose contact elements 361 and 363 thereon, and central portion 336a is then placed on precordium area 326. (If protective covering 365 is of a one piece design, it is removed from all of first surface 341 at this time.) Adhesive first surface 341 of central portion 336a retains it in position on precordium area 326. LA conductive element 361 carried on central portion 336a of strip 336 adjacent $V_6$ conductive element 361 and first end 343 is positioned on strip 336 so as to be near left arm 331 and substitutes for the separate electrode formerly positioned on the left arm of patient 322.

LL and RA conductive elements 361 are positioned on patient 322 by simply pulling extendable portions 336d and 336e from their first position near $V_1$ through $V_6$ and LA conductive elements 361 to their second position remote the $V_1$ through $V_6$ and LA contact elements and near left leg 333 and right arm 328, respectively, of patient 322. More specifically, LL conductive element 361 is placed in a remote position on the lower left thorax and upper left abdomen of patient 322, and RA conductive element 361 is placed in a remote position on the upper right thorax of patient 322. In their remote positions, LL and RA conductive elements 361 constitute "floating" conductive elements.

This pulling of extendable portions 336d and 336e away from central portion 336a to position or place LL conductive element 361 on the lower left thorax and upper left abdomen and RA conductive element 361 on the upper right thorax is permitted by first and second elastic portions 336b and 336c of strip 336 and extendable portions 371a of wires 371. When LL and RA conductive elements 361 are in their remote positions, first and second extendable portions 336d and 336e are each distanced between five and fifteen centimeters from central portion 336a. There is no need for millimetric accuracy in positioning of LL and RA conductive elements 361 carried by extendable portions 336d and 336e.

If protective covering 365 is segmented and not yet been removed, the balance of the protective covering is removed from extendable portions 336d and 336e of strip 336, to expose LL and RA conductive elements 361 and adhesive first surface 341, before placing first and second extendable portions 336d and 336e on patient 322. LL and RA "floating" conductive elements 361 carried by extendable portions 336d and 336e substitute for the separate electrodes formerly positioned on the left leg and right arm of the patient.

It should be appreciated that elastic portions 336b and 336c may be designed to permit extendable portions 336d and 336e to separate and break off from central portion 336a during placement of LL and RA conductive elements 361 on patient 322 and be within the scope of the present invention. The separation of extendable portions 336d and 336e from central portion 336a by causing elastic portions 336b and 336c to break apart can be accomplished by adjusting the elasticity and flexibility of the polyurethane, polyvinyl chloride or other plastic material from which the elastic portions are made. For example, if elastic portions 336b and 336c are made of polyurethane, it is possible to set its hardness scale to be low enough to permit complete separation.

Elastic portions 336b and 336c designed to completely separate from central portion 336a do not cause wires 371 to break or sever. Accordingly, LL and RA conductive elements 361 remain electrically connected and coupled to microchip 372 by respective wires 371. Stretchable portions 371a of wires 371 permit such electrical coupling when LL and RA conductive elements are in their remote "floating" positions.

The inclusion in strip assembly 321 of common reference element 363 eliminates the need for a separate reference electrode on the right leg of patient 322. In addition, reference element 363 is a common reference for all conductive elements 361. As a result, there is no need to electronically or otherwise calculate the reference point during unipolar monitoring. A conductive gel may be applied between each contact element 361 and 363 to enhance the detection of heart signals thereby. Strip assembly 321 may be provided with a microchip 372 which is removable or nonremovable. A removable microchip 372 can be used in multiple monitorings, reducing the cost of an electrocardiographic testing performance.

Upon commencement of monitoring, the twelve lead electrocardiographic monitoring system carried by strip assembly 321 detects heart signals at each of the ten contact elements 361 and 363 to permit complete unipolar and bipolar "leads" views of heart 324 electrical activity. The reference heart signal is detected by reference element 363 incorporated within strip assembly 321. Once detected, the signals are carried through wires 368 and 371 to chip receptacle 366, where they are picked up by pins 373 on microchip 372 which cooperatively mate with pin sockets 367 in the chip receptacle. Microchip 372 combines the heart signals detected by contact elements 361 and 363 into a twelve-lead electrocardiogram configuration. Microchip 372 contains the necessary electronic components for transmitting the multiplexed encoded and modulated twelve-lead electrocardiogram heart signals over a single frequency radio frequency signal. No wires connecting patient 322 to the receiver and decoder portion of the wireless system are needed to permit completion of the electrocardiographic monitoring.

Thus, microchip 372 transmits the twelve-lead electrocardiogram single encoded signal using the information derived from the electrocardiographic twelve-lead "views". The electrocardiogram "lead" is a "view point" from which the electrical activity of the heart is examined. Each view is the result of a combination of two signals at two spaced apart or separated points as measured by two contact elements, such as one conductive element 361 and another conductive element 361 (RA, LA and LL conductive elements 361 which are compared to each other to determine leads I, II and II of the Einthoven triangle bipolar lead system), or a conductive element 361 and common reference element 363 (LA, LL , RA and $V_1$ through $V_6$ conductive elements 361 which are compared to reference element 363 to determine leads aVR, aVL, aVF and $V_1$ through $V_6$ in the unipolar lead system).

Therefore, in this invention, microchip 372 provides the end results of these views or coupled measurements, of which every two contact elements provide a "lead view" while coupling of variable contact elements create, according to electrophysiological principals, the complete "picture" of twelve-lead electrocardiograms. The inclusion by this invention of microchip 372 in strip assembly 321 creates an "active" and "smart" wireless electrode system which permits a "novel" method of electrocardiographic analysis. Under this method, a complete twelve-lead electrocardiogram is created on the patient. This twelve-lead electrocardiogram is created not merely by electrocardiographic hardware, as is done by current and existing electrocardiograph systems. The invention provides a new "smart" method of electrocardiographic data analysis.

During monitoring, patient 322 can ambulate within the approximate 50 to 150 meter transmission range of microchip 372 without interrupting the detection and transmission of twelve-lead electrocardiographic heart signals for analysis. Motion electronic stabilizers may be incorporated or connected to or within microchip 372 in order to optimize "clean" from noise recording of heart signals. These stabilizers may consist of a combination of various filters and similar digital signal stabilizers to eliminate unwanted noise such as artifacts. Furthermore, the unitary structure of strip assembly 321 eliminates the likelihood of interchanging signals and the inaccuracies in the heart signals from faulty wires and wire connections or disconnections.

Figures 22, 23:
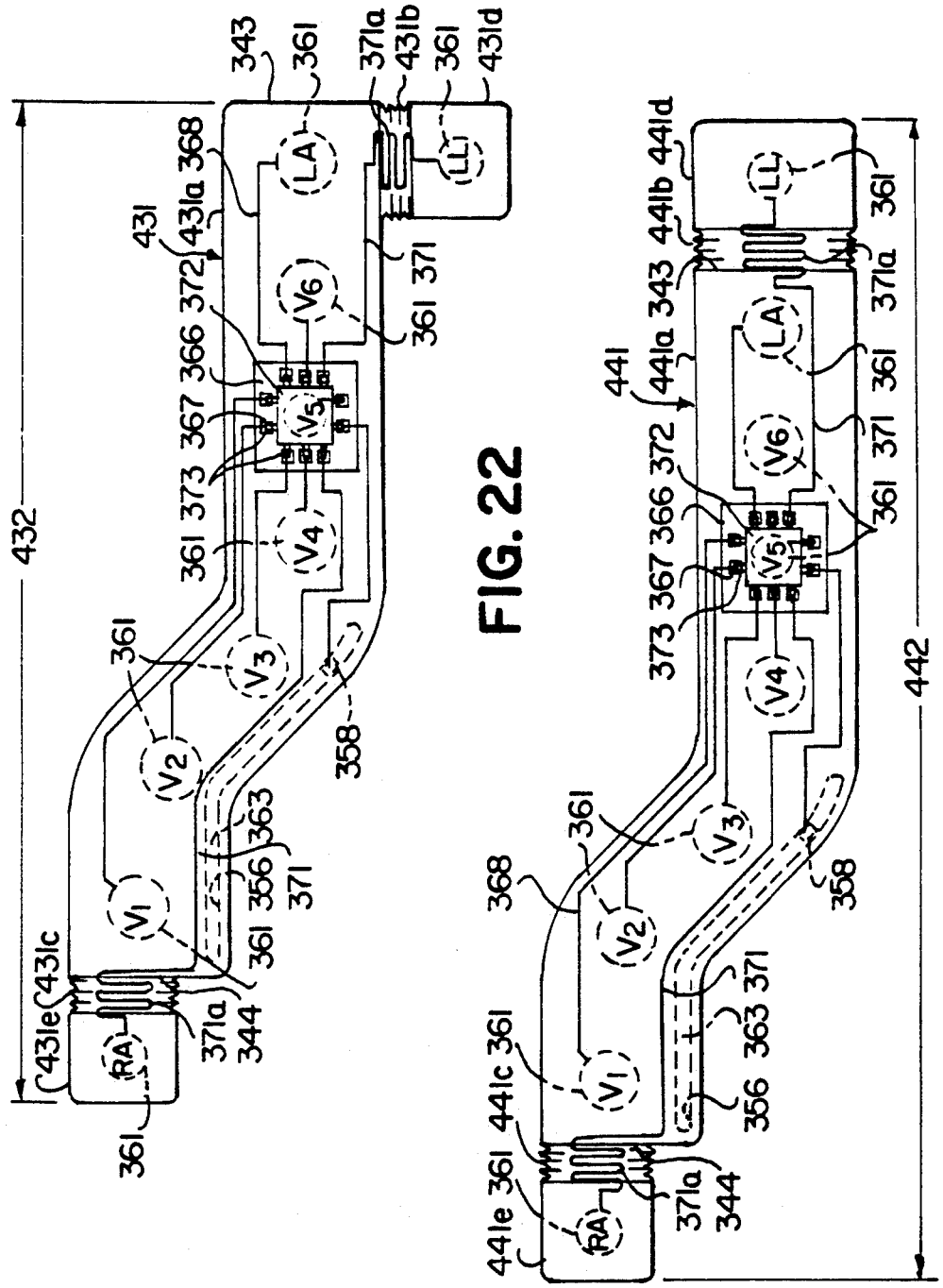
FIG. 22 is a top plan view of another embodiment of a precordial strip assembly, similar to the embodiment shown in FIG. 18, incorporating the present invention.
FIG. 23 is a top plan view of another embodiment of a precordial strip assembly, similar to the embodiment shown in FIG. 18, incorporating the present invention.

In another embodiment, precordial strip assembly 321 includes an elongate strip or strip means 431 generally in the shape of a horizontal inverted "L", and having a length identified by dimension 432 in FIG. 22 and a width and height substantially equal to width 338 and height 339 in FIGS. 18 and 19, respectively. Length 432 can range from five to forty-two centimeters. Strip 431 can be made from the same material as strip 336, and has a central portion 431a, first and second elastic portions 431b and 431c and first and second extendable or stretchable portions 431d and 431e substantially identical to central portion 336a, first and second elastic portions 336b and 336c and first and second extendable portions 336d and 336e of strip 336. Central portion 431a has first or left and second or right ends 343 and 344.

Like central portion 336a, central portion 431a has $V_1$ through $V_6$ and LA conductive contact elements 361 and a reference contact element 363 mounted thereon, and is also provided with a chip receptacle 366 and a microchip 372 thereon. Wires 368 assist in electrically connecting and coupling $V_1$ through $V_6$ and LA conductive elements 361 and reference element 363 to chip receptacle 366. First and second extendable portions 431d and 431e have LL and RA conductive contact elements 361 mounted thereon in the same manner as those elements are mounted on extendable portions 336d and 336e, respectively. Wires 371, with extendable or stretchable portions 371a, assist in electrically connecting and coupling LL and RA conductive elements 361 to chip receptacle 366.

First elastic and extendable portions 431b and 431d are configured with respect to central portion 431a in the same manner as first elastic and extendable portions 336b and 336d are configured with respect to central portion 336a. Second elastic and extendable portions 431c and 43le protrude in a substantially colinear manner from second end 344 of central portion 431a.

In another related embodiment, precordial strip assembly 321 includes an elongate strip or strip means 441 generally linear and horizontal in conformation, and having a length identified by dimension 442 in FIG. 23 and a width and height substantially equal to width 338 and height 339 in FIGS. 18 and 19, respectively. Length 442 can range from five to forty-six centimeters. Strip 441 can be made from the same material as strip 336, and has a central portion 441a, first and second elastic portions 441b and 441c and first and second extendable or stretchable portions 441d and 441e substantially identical to central portion 336a, first and second elastic portions 336b and 336c and first and second extendable portions 336d and 336e of strip 336. Central portion 441a has first or left and second or right ends 343 and 344.

Like central portion 336a, central portion 441a has $V_1$ through $V_6$ and LA conductive contact elements 361 and a reference contact element 363 mounted thereon, and is also provided with a chip receptacle 366 and a microchip 372 thereon. Wires 368 assist in electrically connecting and coupling $V_1$ through $V_6$ and LA conductive elements 361 and reference element 363 to chip receptacle 366. First and second extendable portions 441d and 441e have LL and RA conductive contact elements 361 mounted thereon in the same manner as those elements are mounted on extendable portions 336d and 336e, respectively. Wires 371, with extendable or stretchable portions 371a, assist in electrically connecting and coupling LL and RA conductive elements 361 to chip receptacle 366.

First elastic and extendable portions 441b and 441d protrude in a substantially colinear manner from first end 343 of central portion 441a. Second elastic and extendable portions 441c and 441e protrude in a substantially colinear manner from second end 344 of central portion 441a.

The operation of strip assembly 321 which includes either strip 431 or strip 441 is similar to the operation discussed above with respect to the strip assembly having strip 336. After selecting the proper size strip assembly 321 and placing central portion 431a or 441a on the precordium area 326 of patient 322, LL and RA conductive elements 361 on strip 431 or 441 are positioned on patient 322 near left leg 333 and right arm 328, respectively, of patient 322. More specifically, LL conductive element 361 is placed on the lower left thorax and upper left abdomen of patient 322, and RA conductive element 361 is placed on the upper right thorax of patient 322.

With respect to strip 431, LL conductive element 361 is so positioned by pulling extendable portion 431d downwardly from its first position near $V_1$ through $V_6$ and LA conductive elements 361 to its second position remote the $V_1$ through $V_6$ and LA conductive elements. With respect to strip 441, LL conductive element 361 is so positioned by pulling extendable portion 441d sidewardly and leftwardly from its first position near $V_1$ through $V_6$ and LA conductive elements 361 to its second position remote the $V_1$ through $V_6$ and LA conductive elements. With respect to both strips 431 and 441, RA conductive element 361 is so positioned by pulling extendable portion 43le or 441e sidewardly or rightwardly from its first position near $V_1$ through $V_6$ and LA conductive elements 361 to its second position remote the $V_1$ through $V_6$ and LA conductive elements. In their remote positions, LL and RA conductive elements 361 constitute "floating" conductive elements.

In each instance, the pulling of extendable portions 431d and 43le or 441d and 44le away from central portion 431a or 441a, respectively, is permitted by first and second elastic portions 431b and 431c or 441b and 441c and extendable portions 371a of wires 371. When LL and RA conductive elements 361 are in their remote positions, the extendable portions are each distanced between five and fifteen centimeters from the central portion.

In another embodiment, precordial strip assembly 321 includes an elongate strip or strip means 451 substantially similar to central portion 336a of strip 336. Like strip 336, strip 451 has $V_1$ through $V_6$ and LA conductive contact elements 361 and a reference contact element 363 mounted thereon, and is also provided with a chip receptacle 366 and a microchip 372 thereon (See FIGS. 24 and 25). Microchip 372 includes amplifiers 381 (shown for simplicity as a single amplifier), encoder-modulator 382 (which includes an analog-to-digital converter and a multiplexer), transmitter 383 and wireless-signal radiator or sending antenna 386. Wires 368 assist in electrically connecting and coupling $V_1$ through $V_6$ and LA conductive elements 361 and reference element 363 to chip receptacle 366.

In this embodiment, LL and RA conductive elements 361 are mounted on first and second patches 452 and 453 in the same manner that conductive elements 361 are mounted on strips 336 and 451. Patches 452 and 453 are made of a suitable non-conductive and insulating layer of plastic material which is also flexible. The plastic material may include suitable materials such as polyurethane and/or polyvinyl chloride, or a combination thereof, and may be formed through the processes discussed above to vary in flexibility. Patches 452 and 453 have an adhesive on one surface thereof similar to the adhesive contained on first surface 341 of strip 336. Wires 454, which are thin, conductive and flexible, serve as means for electrically coupling and connecting RA and LL conductive elements 361 to chip receptacle 366. Wire 454 relating to LL patch 452 joins strip 451 near left end 343, while 454 relating to patch 453 joins strip 451 near right end 344. Wires 454 extend from three to fifteen centimeters from strip 451.

RA and LL conductive elements 361 are adapted to contact skin 327 near right arm 328 and left leg 333, respectively, for detecting heart signals from patient 322. More specifically, RA conductive element 361 is positioned on the upper right thorax of the patient, and LL conductive element 361 is positioned on the lower thorax and left upper abdomen of the patient.

The operation of strip assembly 321 which includes strip 451 is similar to the operation discussed above with respect to the strip assembly having strip 336. Patches 452 and 453 are placed on patient 322 in close proximity to strip 451, and wires 454 can serve to define the maximum distance between the patches and strip 451.

In another embodiment, precordial strip assembly 321 includes an elongate strip or strip means 471 which is slightly shorter in length but otherwise substantially similar to central portion 336a of strip 336. Strip 471 has $V_1$ through $V_6$ conductive contact elements 361 mounted thereon, like strip 336, but does not have a LA conductive element or a reference contact element mounted thereon (See FIG. 26). Strip 471 has first or left and second or right ends 472 and 473, and is also provided with a chip receptacle 366 and a microchip 372 thereon. Wires 368 assist in electrically connecting and coupling $V_1$ through $V_6$ conductive elements 361 to chip receptacle 366.

Figures 24, 25:
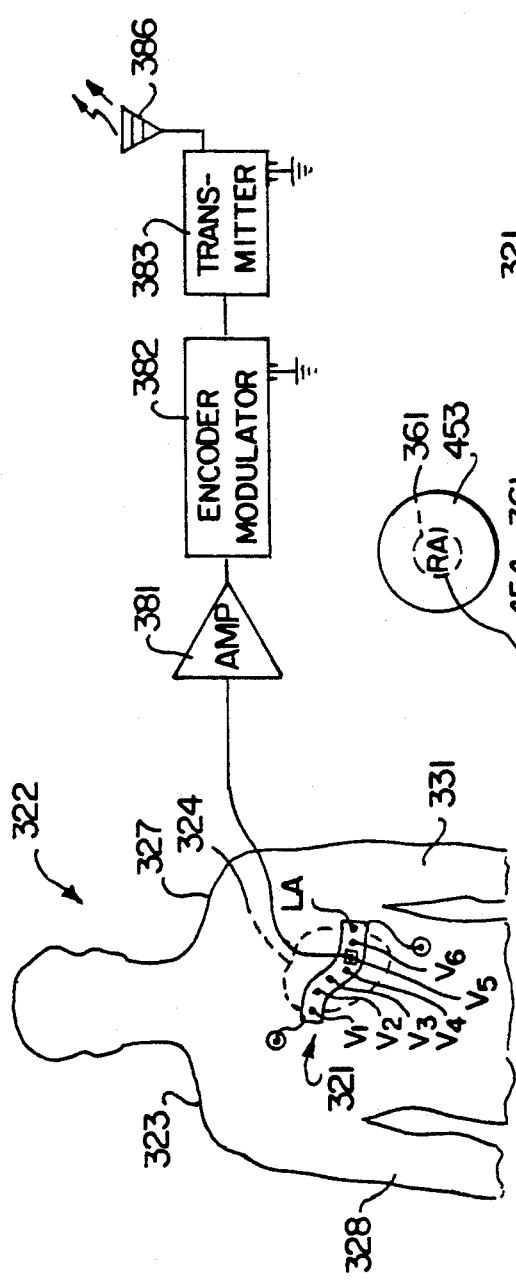
FIG. 24 is a view of another embodiment of a precordial strip assembly for electrocardiographic monitoring placed on the precordium area of a patient, together with a block diagram of a portion of a wireless electrocardiographic monitoring system.
FIG. 25 is a top plan view of another embodiment of a precordial strip incorporating the present invention.

LL and RA conductive elements 361 are mounted on first and second patches 452 and 453, in the same manner as on strip assembly 321 which includes strip 451 illustrated in FIG. 25, and are electrically coupled and connected to chip receptacle 366 by wires 454. In this embodiment, LA conductive element 361 is similarly mounted on a patch 476 and a tenth contact element, reference contact element 477 which is substantially identical in construction to conductive contact elements 361, is also similarly mounted on a patch 478. Patch 478, with conductive element 361 thereon, is sometimes referred to as the RL contact element.

Patches 476 and 478 are made of a suitable non-conductive and insulating layer of plastic material which is also flexible. The plastic material may include suitable materials such as polyurethane and/or polyvinyl chloride, or a combination thereof, and may be formed through the processes discussed above to vary in flexibility. Patches 476 and 478 have an adhesive on one surface thereof similar to the adhesive contained on first surface 341 of strip 336. Wires 481, which are thin, conductive and flexible, serve as means for electrically coupling and connecting LA conductive element 361 and RL reference element 477 to chip receptacle 366. Wire 481 relating to LA patch 476 joins strip 471 near left end 472, while wire 481 relating to patch 478 joins strip 471 near right end 473. Wires 481 extend from three to fifteen centimeters from strip 471.

LA conductive element 361 and RL reference element 477 are adapted to contact skin 327 near left arm 331 and right leg 332, respectively, for detecting heart signals from patient 322. More specifically, LA conductive element 361 is positioned on the upper left thorax of the patient, and RL reference element 477 is positioned on the lower thorax and right upper abdomen of the patient.

The operation of strip assembly 321 which includes strip 471 is similar to the operation discussed above with respect to the strip assembly having strip 336. Patches 452, 453, 476 and 478 are placed on patient 322 in close proximity to strip 471, and wires 454 and 481 can serve to define the maximum distance between the patches and strip 471.

In another embodiment of strip assembly 321, a strip 488, substantially similar to central portion 336a but without chip receptacle 366 and microchip 372, includes cable means for carrying the heart signals detected by contact elements 361 and 363 to the monitor and related analysis equipment. Strip 488 has first or left and second or right ends 489 and 490. In this embodiment, illustrated in FIG. 27, the junction means is comprised of a cable jacket 491 being carried in a single region near first end 489 of strip 488 and having a plug 492 on the end thereof. Strip 488 has wires 493 which, together with cylindrical conductive pads 348 and conductive pad 358, serve as means for electrically coupling and connecting conductive elements 361 and reference element 363, respectively, to cable jacket 491. Cable 494 serves as the cable means and connects to plug 492. Strip assembly 321 of this embodiment could include elastic and extendable portions similar to elastic portions 336b and 336c and extendable portions 336d and 336e or patches similar to patches 452, 453 and 476 for carrying LL, RA and/or LA conductive elements 361 or similar to patch 478 for carrying reference element 477 and be within the scope of the present invention.

Precordial strip assembly 321 utilizes the method and system of electrocardiographic monitoring in which the detection and processing of a twelve-lead electrocardiogram is performed and accomplished on the body of patient 322 (See FIG. 28). As more fully discussed above, conductive contact elements 361, together with common reference contact element 363 or 477, detect heart signals which correspond to traditional precordial detection points $V_1$ through $V_6$ and limb detection points LA, LL, RA and RL. These heart signals are analyzed and coupled, by microchip 372, to create the aVR, aVL and aVF limb leads and precordial leads $V_1$ through $V_6$ of the unipolar lead system and leads I, II and III of the bipolar lead system. Microchip 372 can also serve as means for transmitting the electrocardiogram over a radio frequency signal. More specifically, microchip 372 serves to digitize and combine the multichannel twelve-lead electrocardiogram into a time multiplexed signal and send the combined signal over a single transmission frequency.

One of the approaches suggested by the wireless electrocardiographic monitoring system (WEMS) of the invention is to eliminate the physical wires between the patient and the electrocardiograph and monitor and to provide a complete standard twelve-lead electrocardiogram with only one electrode strip. This approach has the potential to greatly enhance the practicality of and simplify the use of electrocardiographic equipment and significantly improve clinical care of patients affected by heart disease. In addition, a wireless electrocardiographic monitoring system would expand the use of complete standard twelve-lead electrocardiograms. This may significantly improve control modalities for the diagnosis and therapy of critically ill cardiac patients that require and benefit from maximal electrophysiological activities detection and evaluation not available with currently existing methods and clinical management protocols which employ only single-lead or three-lead arrhythmia monitoring.

A wireless electrocardiographic monitoring system would permit early detection of unrecognized myocardial ischemia while a patient is in a coronary intensive care or intensive care unit and, accordingly, expand diagnostic accuracy and specifically determine the urgency and/or the need for other therapeutic modalities such as medication (including anticoagulants and thrombolytic drugs), angiography, percutaneous transluminal coronary angioplasty or coronary artery bypass graft surgery.

A wireless electrocardiographic monitoring system would also enable accurate detection of myocardial ischemia during percutaneous transluminal coronary angioplasty. An accurate detection would maximize diagnosis efficacy and improve therapy effectiveness, and possibly result in modification of the percutaneous transluminal coronary angioplasty procedure itself. The system would precisely determine the severity and location of the ischemic event and be critical for deciding whether to repeat the angioplasty procedure in the coronary artery and/or to modify treatment protocol with adjunctive medications (e.g., vasodilators, anticoagulants or thrombolytic drugs) and/or coronary artery bypass graft surgery. It should also be noted that there is preliminary evidence to suggest that early detection of myocardial ischemia may be an important predictor in the development of restenosis following percutaneous transluminal coronary angioplasty of the coronary arteries.

In addition, complete standard twelve-lead electrocardiographic recordings taken during percutaneous transluminal coronary angioplasty could function as an individualized noninvasive template or "fingerprint", useful in evaluating transient ischemic episodes after the patient leaves the cardiac catheterization laboratory. Occasionally, an acute myocardial infarction develops spontaneously in the hours after elective percutaneous transluminal coronary angioplasty. Use of continuous complete standard twelve-lead electrocardiograms would facilitate comparisons between the dynamic changes of the "controlled" ischemic period during the percutaneous transluminal coronary angioplasty procedure (as baseline value) and the ischemic period during the evolving MI (rather than observing changes in numbers of millimeters). Such information may provide a more complete understanding of the evolution of the acute ischemic process, which may be critical for therapeutic considerations.

Complete twelve-lead electrocardiograms by a wireless electrocardiographic monitoring system would also expand the field of diagnosis and therapy of silent coronary ischemia in the ambulatory setting. By providing an accurate and complete ambulatory method of detecting silent ischemia, it could direct to early and accurate therapy (medication, invasive intervention and/or surgery), thereby increasing significantly the efficacy of therapy and reducing morbidity and mortality rates of heart disease.

A wireless electrocardiographic monitoring system would also be a comprehensive and reliable ambulatory tool for providing accurate detection, 24 hours a day, upon demand and in real time occurrence, of coronary ischemia in high risk cardiac patients who must transmit electrocardiograms transtelephonically.

The complete standard twelve-lead electrocardiogram, detected by the wireless electrocardiographic monitoring system of the invention, would be recorded by a currently available beeper-size twelve-lead electrocardiogram recorder and transmitter carried by the patient and be transmitted by the patient through any telephone line to a cardiac monitoring control center. This system would expand the quality of heart disease control and detection capabilities and, in addition, would direct to better accuracy of treatment, whether it be medication, invasive intervention or urgent surgery.

Furthermore, this transtelephonic method would significantly extend the control and improve the follow-up of a significant number of patients affected by heart disease, with both enhanced efficacy and efficiency of treatment. A complete standard twelve-lead electrocardiogram detection in high risk patients, 24 hours a day and upon demand, has the potential of greatly decreasing the heart disease mortality rate.

A wireless electrocardiographic monitoring system could provide complete standard twelve-lead electrocardiograms in coronary intensive care mobil units and emergency rooms for early accurate myocardial ischemia detection and diagnosis, and thus improve therapeutic management and the administration of thrombolytic or anticoagulative drugs in the early stages of a coronary ischemic event. In addition, the system could direct to more accurate therapy (e.g., percutaneous transluminal coronary angioplasty or coronary artery bypass graft surgery), if necessary, during hospitalization.

In patients with acute myocardial infarction who undergo thrombolytic reperfusion therapy, monitoring ST-segment deviation could provide an early noninvasive indicator of coronary artery reocclusion not available from current coronary care electrocardiographic monitoring aimed at the detection of cardiac arrhythmias. A twelve-lead electrocardiogram can, therefore, identify patients who may require further pharmacological treatment to prevent reocclusion of the coronary artery, or who may require subsequent invasive investigation before coronary angioplasty or bypass surgery for residual coronary arterial stenosis.

Intraoperative twelve-lead electrocardiograms would diagnose accurately more postoperative myocardial ischemia than any other monitoring modality. It is noninvasive, and would allow preoperative, intraoperative and postoperative electrocardiographic monitoring to proceed without interruption.

In view of the foregoing, the wireless electrocardiographic monitoring system of the present invention overcomes practical difficulties in existing electrocardiographic monitoring systems. It accomplishes this by, for example:

1. Reducing significantly the number of electrodes required to obtain a complete standard twelve-lead electrocardiogram;

2. Eliminating the time spent connecting predetermined multiple wires to predetermined multiple electrodes;

3. Eliminating wire connection errors;

4. Eliminating the time spent untangling wires;

5. Simplifying the method of operation when used by a coronary intensive care mobile unit where speed of operation is critical;

6. Reducing or eliminating wire defects that are often difficult to detect;

7. Reducing or eliminating problems relating to the wire connections at electrodes;

8. Reducing or eliminating problems relating to wire disconnections occurring beneath the sterile field during operating room surgical procedures;

9. Reducing cardiac monitoring interruptions by ambulating patients in the intermediate coronary unit;

10. Improving clinical care management as standard complete twelve-lead electrocardiograms would be available for detection of myocardium ischemia during and following percutaneous transluminal coronary angioplasty, percutaneous laser coronary angioplasty procedures, percutaneous coronary retroperfusion, coronary artery bypass graft surgery, and thrombolytic therapy (Currently, only single-lead or three-lead arrhythmia monitoring is performed with these procedures.);

11. Making possible portable transtelephonic wireless twelve-lead electrocardiographic monitoring;

12. Eliminating proximity limitations between the patient and currently operated electrocardiographs or monitors; and 13. Increasing patient's compliance (comfort level) when twelve-lead electrocardiographic testing is required (i.e., when sleeping or already connected to other instrumentation as in a coronary intensive care unit).

Also in view of the foregoing, it can be seen that the new precordial strip assembly of the present invention is a significant improvement over the prior art. The strip assembly contains a plurality of conductive elements for placement on the precordium area of a patient, and includes a reference conductive element permitting elimination of the standard right leg reference electrode. The strip assembly serves as an "active" electrode, as opposed to "passive" electrodes currently used for electrocardiographic testing. The strip assembly includes RA and LL conductive elements positionable on the patient in a position remote from the $V_1$ through $V_6$ and LA conductive elements. The invention provides a self contained strip assembly for detecting and transmitting twelve-lead electrocardiogram heart signals.

While particular embodiments have been shown and described, it will be apparent to those skilled in the art that variations and modifications may be made in these embodiments without departing from the spirit and scope of this invention. It is the purpose of the appended claims to cover any and all such variations and modifications.

What is claimed is:

1. A wireless electrocardiographic monitoring system, including:
   right arm, left arm and left leg dipole electrodes for attachment to right arm, left arm and left leg limbs, respectively of a patient;
   right arm heart signal transmitting means mounted on said right arm electrode for radiating a signal corresponding to the heart signal at said right arm electrode;
   left arm heart signal transmitting means on said left arm electrode for radiating a signal corresponding to the heart signal at said left arm electrode;
   left leg heart signal transmitting means on said left arm electrode for radiating a signal corresponding to the heart signal at said left arm electrode;
   a plurality of signal receiving means, one each for receiving and detecting said radiated heart signals from said left arm, right arm and left leg electrodes, respectively, to individually produce a received left arm heart signal, a received right arm heart signal and a received left leg heart signal;
   means for combining said individually received left arm, right arm and left leg heart signals to produce a reference potential;
   a set of precordial dipole electrodes for attachment to the chest of a patient;
   a set of precordial heart signal transmitting means mounted on each of said precordial dipole electrodes in said set, respectively for individually transmitting signals corresponding to the heart signal at respective ones of said precordial electrodes;
   a set of precordial heart signal receiving and detecting means, each one associated with a different one of said precordial heart signal transmitting means for individually reproducing the heart signals appearing at each of said precordial electrodes in said set;
   signal display means;
   means for coupling said detected heart signals e aid right arm, left arm and left leg electrodes and from said precordial electrodes to said signal display means; and
   means for providing operating power for all of the foregoing.

2. System according to claim 1 in which each of said right arm, left arm, left leg and precordial dipole electrodes comprises first and second conductive elements spaced-apart from each other.

3. A wireless electrocardiographic monitoring system, including:
   right arm, left arm and left leg dipole electrodes for attachment to right arm, left arm and left leg limbs, respectively of a patient;
   right arm heart signal transmitting means mounted on said right arm electrode for radiating a signal corresponding to the heart signal at said right arm electrode;
   left arm heart signal transmitting means on said left arm electrode for radiating a signal corresponding to the heart signal at said left arm electrode;
   left leg heart signal transmitting means on said left arm electrode for radiating a signal corresponding to the heart signal at said left arm electrode;
   a plurality of signal receiving means, one each for receiving and detecting said radiated heart signals from said left arm, right arm and left leg electrodes, respectively, to individually produce a received left arm heart signal, a received right arm heart signal and a received left leg heart signal;
   means for combining said individually received left arm, right arm and left leg heart signals to produce a reference potential;
   a set of precordial dipole electrodes for attachment to the chest of a patient, each of said right arm, left arm, left leg and precordial dipole electrodes including first and second conductive elements spaced-apart from each other and each of said transmitting means including noise reduction means coupled to said second conductive element for detecting background noise, differential input amplifier means having a non-inverting input terminal coupled to said first conductive element and an inverting terminal coupled to said noise reduction means for subtracting the background noise signal from the signal present on said first conductive element;
   a set of precordial heart signal transmitting means mounted on each of said precordial dipole electrodes in said set, respectively for individually transmitting signals corresponding to the heart signal at respective ones of said precordial electrodes;

a set of precordial heart signal receiving and detecting means, each one associated with a different one of said precordial heart signal transmitting means for individually reproducing the heart signals appearing at each of said precordial electrodes in said set;

signal display means;

means for coupling said detected heart signals from said right arm, left arm and left leg electrodes and from said precordial electrodes to said signal display means; and means for providing operating power for all of the foregoing.

4. System according to claim 1 in which said means for providing operating power includes a battery and battery switching means in each of said left arm, right arm, left leg and precordial transmitting means.

5. System according to claim 4 in which said battery switching means includes a removable insulator which when present maintains the battery disconnected.

6. System according to claim 1 further including an LED and LED driver as part of each of said left arm, right arm, left leg and precordial transmitting means for indicating the presence of signals.

7. System according to claim 1 wherein said set of precordial electrodes includes a strip means of a selected length for capturing said precordial dipole electrodes in a linear array spaced-apart from each other.

8. System according to claim 7 wherein each dipole electrode of said strip means includes first and second conductive elements spaced-apart from each other.

9. System according to claim 7 wherein said strip means includes adhesive means for affixing same to the chest of the patient and retaining it in a desired location.

10. System according to claim 7 wherein said strip means includes a body portion that is elastic to permit stretching thereof to the length necessary to span the patient's chest from substantially the sternum to the left side.

11. A wireless electrocardiographic monitoring system, including:

right arm, left arm, right leg and left leg electrodes for attachment to right arm, left arm, right leg and left leg limbs, respectively of a patient;

an elongate strip for attachment to the chest of the patient, a set of aligned precordial electrodes carried by said strip;

heart signal transmitting means coupled to said right and left arm and right and left leg electrodes and said set of precordial electrodes for transmitting signals corresponding to the heart signals at said right arm, left arm, right leg, left leg and precordial electrodes;

signal receiving means for receiving and detecting said transmitted heart signals to produce a received left arm heart signal, a received right arm heart signal, a received right leg heart signal, a received left leg heart signal and received precordial signals;

signal display means;

means for coupling said detected heart signals from said right arm, left arm, right leg and left leg electrodes and from said precordial electrodes to said signal display means; and means for providing operating power for all of the foregoing.

12. System according to claim 11 wherein the transmitting means and the receiving means utilize a center frequency.

13. A wireless electrocardiographic monitoring system, including:

right arm, left arm, right leg, and left leg electrodes for attachment to right arm, left arm, right leg and left leg limbs, respectively of a patient;

right arm heart signal transmitting means mounted on said right arm electrode for radiating a signal corresponding to the heart signal at said right arm electrode;

left arm heart signal transmitting means on said left arm electrode for radiating a signal corresponding to the heart signal at said left arm electrode;

left leg heart signal transmitting means mounted on said left leg electrode for radiating a signal corresponding to the heart signal at said left leg electrode;

a plurality of signal receiving means, one each for receiving and detecting said radiated heart signals from said left arm, right arm and left leg electrodes, respectively, to individually produce a received left arm heart signal, a received right arm heart signal and a received left leg heart signal;

means for combining said individually received left arm, right arm and left leg heart signals to produce a reference potential;

reference potential transmitting means coupled to said combining means for transmitting said reference potential;

right leg signal receiving means electrically couplable to said right leg electrode for receiving said reference potential and applying said reference potential to said right leg electrode;

a set of precordial electrodes for attachment to the chest of a patient;

a set of precordial heart signal transmitting means mounted on each of said precordial electrodes in said set, respectively, for individually transmitting signals corresponding to the heart signal at respective ones of said precordial electrodes;

a set of precordial heart signal receiving and detecting means, each one associated with a different one of said precordial heart signal transmitting means for individually reproducing the heart signals appearing at each of said precordial electrodes in said set;

signal display means;

means for coupling said detected heart signals from said right arm, left arm and left leg electrodes and from said precordial electrodes to said signal display means; and means for providing operating power for all of the foregoing;

wherein each transmitting means and associated receiving means has the same digital encoding, and the digital encoding of each transmitting means is unique.

14. System according to claim 13 wherein each transmitting means and receiving means includes adjustment means for varying said digital encoding.

15. A wireless electrocardiographic monitoring system, including:

right arm, left arm and left leg dipole electrodes for attachment to right arm, left arm and left leg limbs, respectively of a patient;

right arm heart signal transmitting means mounted on said right arm electrode for transmitting a signal corresponding to the heart signal at said right arm electrode;

left arm heart signal transmitting means mounted on said left arm electrode for transmitting a signal corresponding to the heart signal at said left arm electrode;

left leg heart signal transmitting means mounted on said left leg electrode for transmitting a signal corresponding to the heart signal at said left leg electrode;

a plurality of signal receiving means, one each for receiving and detecting said transmitted heart signals from said left arm, right arm and left leg electrodes to individually produce a received left arm heart signal, a received right arm heart signal and a received left leg heart signal;

a set of precordial electrodes for attachment to the chest of a patient;

a set of precordial heart signal transmitting means mounted on each of said precordial electrodes in said set, respectively for individually transmitting signals corresponding to the heart signal at respective ones of said precordial electrodes;

a set of precordial heart signal receiving and detecting means, each one associated with a different one of said precordial heart signal transmitting means for individually reproducing the heart signals appearing at each of said precordial electrodes in said set;

means for providing operating power for all of the foregoing; and means for selectively coupling said detected heart signals from said right arm, left arm and left leg electrodes from said precordial electrodes to an electrocardiographic recorder.

16. System according to claim 15 in which each of said right arm, left arm, left leg and precordial electrodes comprises first and second conductive elements spaced-apart from each other.

17. A wireless electrocardiographic monitoring system, including:

right arm, left arm and left leg dipole electrodes for attachment to right arm, left arm and left leg limbs, respectively of a patient;

right arm heart signal transmitting means mounted on said right arm electrode for transmitting a signal corresponding to the heart signal at said right arm electrode;

left arm heart signal transmitting means mounted on said left arm electrode for transmitting a signal corresponding to the heart signal at said left arm electrode;

left leg heart signal transmitting means mounted on said left leg electrode for transmitting a signal corresponding to the heart signal at said left leg electrode;

a plurality of signal receiving means, one each for receiving and detecting said transmitted heart signals from said left arm, right arm and left leg electrodes to individually produce a received left arm heart signal, a received right arm heart signal and a received left leg heart signal;

a set of precordial electrodes for attachment to the chest of a patient, each of said right arm, left arm, left leg and precordial electrodes including first and second conductive elements spaced-apart from each other and each of said transmitting means including noise coil means coupled to said second conductive element for detecting background noise, differential input amplifier means having a noninverting input terminal coupled to said first conductive element and an inverting terminal coupled to said noise coil means for subtracting the background noise signal from the signal present on said first conductive element;

a set of precordial heart signal transmitting means mounted on each of said precordial electrodes in said set, respectively for individually transmitting signals corresponding to the heart signal at respective ones of said precordial electrodes;

a set of precordial heart signal receiving and detecting means, each one associated with a different one of said precordial heart signal transmitting means for individually reproducing the heart signals appearing at each of said precordial electrodes in said set;

means for providing operating power for all of the foregoing; and means for selectively coupling said detected heart signals from said right arm, left arm and left leg electrodes from said precordial electrodes to an electrocardiographic recorder.

18. System according to claim 15 in which said means for providing operating power includes a battery and battery switching means in each of said left arm, right arm, left leg and precordial transmitting means.

19. System according to claim 18 in which said battery switching means includes a removable insulator which when present maintains the battery disconnected.

20. System according to claim 15 further including an LED and LED driver as part of each of said left arm, right arm, left leg and precordial transmitting means for indicating the presence of signals.

21. System according to claim 15 wherein each transmitting means and associated receiving means has the same digital encoding, and the digital encoding of each transmitting means in unique.

22. System according to claim 21 wherein each transmitting and receiving means includes adjustment means for varying said digital encoding.

23. A wireless electrocardiographic monitoring system, including:

right arm, left arm and left leg electrodes for attachment to right arm, left arm and left leg limbs, respectively of a patient;

right arm heart signal transmitting means mounted on said right arm electrode for transmitting a signal corresponding to the heart signal at said right arm electrode;

left arm heart signal transmitting means mounted on said left arm electrode for transmitting a signal corresponding to the heart signal at said left arm electrode;

left leg heart signal transmitting means mounted on said left leg electrode for transmitting a signal corresponding to the heart signal at said left leg electrode;

a plurality of signal receiving means, one each for receiving and detecting said transmitting heart signals from said left arm, right arm and left leg electrodes to individually produce a received left arm heart signal, a received right arm heart signal and a received left leg heart signal;

a set of precordial electrodes for attachment to the chest of a patient;

a set of precordial heart signal transmitting means mounted on each of said precordial electrodes in said set, respectively for individually transmitting signals corresponding to the heart signal at respective ones of said precordial electrodes;

a set of precordial heart signal receiving and detecting means, each one associated with a different one of said precordial heart signal transmitting means for individually reproducing the heart signals appearing at each of said precordial electrodes in said set;

means for providing operating power for all of the foregoing; and means for selectively coupling said detected heart signals from said right arm, left arm and left leg electrodes from said precordial electrodes to an electrocardiographic recorder;

wherein a center frequency of each transmitting means and associated receiving means is the same, and the center frequency of each transmitting means is unique.

24. System according to claim 23 wherein each transmitting means and receiving means includes adjustment means for varying said center frequency.

25. System according to claim 15 wherein said set of precordial electrodes includes a strip means of a selected length for capturing said precordial electrodes in a linear array spaced-apart from each other.

26. System according to claim 25 further including an LED and LED driver as part of each of said left arm, right arm, left leg and precordial transmitting means for indicating the presence of signals.

27. System according to claim 25 wherein each electrode of said strip means includes first and second conductive elements spaced apart from each other to form a dipole electrode.

28. System according to claim 25 in which said means for providing operating power includes a battery and battery switching means in each of said left arm, right arm, left leg and precordial transmitting means.

29. System according to claim 28 in which said battery switching means includes a removable insulator which when present maintains the battery disconnected.

30. System according to claim 25 wherein said strip means includes adhesive means for affixing same to the chest of the patient and retaining it in a desired location.

31. System according to claim 25 wherein said strip means includes a body portion that is elastic to permit stretching thereof to the length necessary to span the patient's chest from substantially the sternum to the left side.

32. A wireless electrocardiographic monitoring system, including:

right arm and left leg electrodes for attachment to right arm and left leg limbs of a patient;

right arm heart signal transmitting means mounted on said right arm electrode for transmitting a signal corresponding to the heart signal at said right arm electrode;

left leg heart signal transmitting means mounted on said left leg electrode for transmitting a signal corresponding to the heart signal at said left leg electrode;

a pair of signal receiving means, one each for receiving and detecting said radiated heart signals from said right arm and left leg electrodes to individually produce a received right arm heart signal and a received left leg heart signal;

strip means of a selected length including a set of precordial electrodes and a left side electrode for attachment to the chest of the patient for capturing said precordial and left side electrodes in a linear array spaced-apart from each other which when placed on the chest of the patient extend from substantially the center of the chest to the left side;

a set of precordial and left side heart signal transmitting means mounted on said precordial and left side electrodes in said set, respectively for individually transmitting signals corresponding to the heart signal at respective ones of said precordial and left side electrodes;

a set of precordial and left side heart signal receiving and detecting means, each one associated with a different one of said precordial and left side heart signal transmitting means for individually reproducing the heart signals appearing at each of said precordial and left side electrodes;

network means for combining said individually received left arm, right arm and left side heart signals to provide a reference potential;

means for providing operating power for all of the foregoing; and means for selectively coupling said detected heart signals from said right arm, left arm and left side electrodes from said precordial electrodes to an electrocardiographic recorder.

33. System according to claim 32 in which said heart signal transmitting means includes an FM transmitter.

34. System according to claim 32 in which said means for providing operating power includes a battery and battery switching means in each of said left arm, right arm, left leg and precordial transmitting means.

35. System according to claim 34 in which said battery switching means includes a removable insulator which when present maintains the battery disconnected.

36. System according to claim 32 further including an LED and LED driver as part of each of said left arm, right arm, left leg and precordial transmitting means for indicating the presence of signals.

37. System according to claim 32 wherein said strip means includes adhesive means for affixing same to the chest of the patient and retaining it in a desired location.

38. System according to claim 32 wherein said strip means includes a body portion that is elastic to permit stretching thereof to the length necessary to span the patient's chest from substantially the sternum to the left side.

39. A wireless electrocardiographic monitoring system, including:

right arm and left leg electrodes for attachment to right arm and left leg limbs of a patient;

right arm heart signal transmitting means mounted on said right arm electrode for transmitting a signal corresponding to the heart signal at said right arm electrode;

left leg heart signal transmitting means mounted on said left leg electrode for transmitting a signal corresponding to the heart signal at said left leg electrode;

a pair of signal receiving means, one each for receiving and detecting said radiated heart signals from said right arm and left leg electrodes to individually produce a received right arm heart signal and a received left leg heart signal;

strip means of a selected length including a set of precordial electrodes and a left side electrode for attachment to the chest of the patient for capturing said precordial and left side electrodes in a linear array spaced-apart from each other which when placed on the chest of the patient extend from substantially the center of the chest to the left side;

a set of precordial and left side heart signal transmitting means mounted on said precordial and left side electrodes in said set, respectively for individually transmitting signals corresponding to the heart signal at respective ones of said precordial and left side electrodes;

a set of precordial and left side heart signal receiving and detecting means, each one associated with a different one of said precordial and left side heart signal transmitting means for individually reproducing the heart signals appearing at each of said precordial and left side electrodes;

network means for combining said individually received left arm, right arm and left side heart signals to produce a reference potential;

means for providing operating power for all of the foregoing; and means for selectively coupling said detected heart signals from said right arm, left arm and left side electrodes from said precordial electrodes to an electrocardiographic recorder;

wherein a center frequency of each transmitting means and associated receiving means is the same, and the center frequency of each transmitting means is unique.

40. System according to claim 39 wherein each transmitting means and receiving means includes adjustment means for varying said center frequency.

41. System according to claim 32 wherein each transmitting means and associated receiving means has the same digital encoding, and the digital encoding of each transmitting means is unique.

42. System according to claim 41 wherein each transmitting means and receiving means includes adjustment means for varying said digital encoding.

43. System according to claim 32 wherein each of said electrodes comprises first and second conductive elements spaced-apart from each other.

44. A wireless electrocardiographic monitoring system, including:

right arm and left leg electrodes for attachment to right arm and left leg limbs of a patient;

right arm heart signal transmitting means mounted on said right arm electrode for transmitting a signal corresponding to the heart signal at said right arm electrode;

left leg heart signal transmitting means mounted on said left leg electrode for transmitting a signal corresponding to the heart signal at said left leg electrode;

a pair of signal receiving means, one each for receiving and detecting said radiated heart signals from said right arm and left leg electrodes to individually produce a received right arm heart signal and a received left leg heart signal;

strip means of a selected length including a set of precordial electrodes and a left side electrode for attachment to the chest of the patient for capturing said precordial and left side electrodes in a linear array spaced-apart from each other which when placed on the chest of the patient extend from substantially the center of the chest to the left side;

a set of precordial and left side heart signal transmitting means mounted on said precordial and left side electrodes in said set, respectively for individually transmitting signals corresponding to the heart signal at respective ones of said precordial and left side electrodes, each of said electrodes including first and second conductive elements spaced-apart from each other and each of said transmitting means including noise reduction means coupled to said second conductive element for detecting background noise, differential input amplifier means having a non-inverting input terminal coupled to said first conductive element and an inverting terminal coupled to said noise reduction means for subtracting the background noise signal from the signal present on said first conductive element;

a set of precordial and left side heart signal receiving and detecting means, each one associated with a different one of said precordial and left side heart signal transmitting means for individually reproducing the heart signals appearing at each of said precordial and left side electrodes;

network means for combining said individually received left arm, right arm and left side heart signals to provide a reference potential;

means for providing operating power for all of the foregoing; and means for selectively coupling said detected heart signals from said right arm, left arm and left side electrodes from said precordial electrodes to an electrocardiographic recorder.

45. An electrode structure for use in a wireless patient monitoring system, including:

non-conductive strip means of selected length and width for supporting a plurality of signal transmitters on one side thereof and an equal plurality of conductive element pairs on the other side thereof, each of said conductive element pairs being in spaced relationship to each other and exposed on said other side of said strip means; and a plurality of transmitter means mounted on said other side of said strip means, each transmitter for monitoring a different signal, each transmitter means including:

battery means having at least one voltage terminal and a ground terminal carried on said one side of said strip means;

a microchip amplifier carried on said other side of said strip means and having a signal input terminal coupled to a first conductive element of a corresponding pair of conductive elements for receiving heart signals therefrom and having an output terminal;

a microchip encoder-modulator carried on said other side of said strip means and having an input terminal coupled to said output terminal of said amplifier and having an output terminal;

a microchip transmitter carried by said strip means on said other side thereof and having an input terminal and an output terminal, said input terminal of said transmitter being coupled to said output terminal of said encoder-modulator;

a wireless-signal radiator having an input terminal coupled to said output terminal of said microchip transmitter;

means for applying operating potentials from said battery to said microchip amplifier, encoder-modulator and transmitter, respectively, of each transmitter means; and means for coupling said ground terminal of said battery to said second conductive element of each pair of conductive elements.

46. Apparatus according to claim 45 wherein said transmitter of each of said plurality of transmitter means includes adjustment means for varying the frequency of operation of each transmitter.

47. Apparatus according to claim 45 wherein said encoder-modulator of each of said plurality of transmitter means includes adjustment means for varying the digital encoding of each encoder-modulator.

48. An electrode structure for use in a wireless patient monitoring system, including:

non-conductive strip means of selected length and width for supporting a plurality of signal transmitters on one side thereof and an equal plurality of conductive element pairs on the other side thereof, each of said conductive element pairs being in spaced relationship to each other and exposed on said other side of said strip means; and a plurality of transmitter means mounted on said other side of said strip means, each transmitter for monitoring a different signal, each transmitter means including:

battery means having at least one voltage terminal and a ground terminal carried on said one side of said strip means;

a microchip amplifier carried on said other side of said strip means and having a signal input terminal coupled to a first conductive element of a corresponding pair of conductive elements for receiving heart signals therefrom and having an output terminal, said amplifer including noise coil means coupled to the second conductive element of the corresponding pair of conductive elements for detecting background noise, differential input amplifer means having a non-inverting input terminal coupled to said first conductive element of the corresponding pair of conductive elements and an inverting terminal coupled to said noise coil means for subtracting the background noise signal from the signal present on said first conductive element of the corresponding pair of conductive elements;

a microchip encoder-modulator carried on said other side of said strip means and having an input terminal coupled to said output terminal of said amplifer and having an output terminal;

a microchip transmitter carried by said strip means on said other side thereof and having an input terminal and an output terminal, said input terminal of said transmitter being coupled to said output terminal of said encoder-modulator;

a wireless-signal radiator having an input terminal coupled to said output terminal of said microchip transmitter;

means for applying operating potentials from said battery to said microchip amplifier, encoder-modulator and transmitter, respectively, of each transmitter means; and means for coupling said ground terminal of said battery to said second conductive element of each pair of conductive elements.

49. A strip assembly for placement on the chest of a patient having a heart with a precordium lying thereover, skin and right and left arms and legs comprising an elongate strip having first and second surfaces, six conductive contact elements identified as $V_1$ through $V_6$ being mounted in spaced apart positions along the length of said strip, said $V_1$ through $V_6$ conductive contact elements being exposed on the first surface of said strip and being adapted to contact said patient's precordium, additional conductive contact elements identified respectively as LA and LL mounted on said strip near said $V_6$ conductive contact element, said LA and LL conductive contact elements being exposed on the first surface of said strip and being adapted to contact said patient's skin near said left arm and left leg respectively, an additional conductive contact element identified as RA mounted on said strip near said $V_1$ conductive contact element, said RA conductive contact element being exposed on the first surface of said strip and being adapted to contact said patient's skin near said right arm, said strip being substantially continuous between said conductive contact elements, a reference contact element mounted on said strip and serving as a common reference for each of said $V_1$ through $V_6$, LA, LL and RA conductive contact elements, said reference contact element being exposed on the first surface of said strip and being adapted to contact said patient's skin, said contact elements capable of detecting heart signals from said patient to produce a twelve-lead electrocardiogram, and conductor means connected to said conductive contact elements and said reference contact element to permit electrical transmission of said detected heart signals.

50. A strip assembly as in claim 49 together with electrical cable means connected to said conductor means for carrying the heart signals detected by said contact elements.

51. A strip assembly as in claim 49 wherein said strip includes stretchable means to permit spacing of a conductive contact element between a first position in close proximity with an adjacent conductive contact element and a second position remote from said adjacent conductive contact element.

52. A precordial strip assembly as in claim 49 together with a microchip mounted on said strip in electrical contact with said conductor means, said microchip including means for transmitting a radio frequency signal which carries the heart signals detected by said contact elements.

53. A precordial strip assembly as in claim 49 wherein said RA, $V_1$ through $V_6$, LA and LL conductive contact elements are respectively spaced apart along said continuous strip.

54. A precordial strip assembly for use on a patient having a heart with a precordium lying thereover, skin and right and left arms and legs comprising an elongate strip having first and second surfaces, six conductive contact elements identified as $V_1$ through $V_6$ mounted in spaced apart positions along the length of said strip, said conductive contact elements being exposed on the first surface of said strip and being adapted to contact said patient's skin for detecting heart signals from said patient when said precordial strip assembly is placed on the precordium of the patient, a microchip mounted on said strip and conductor means electrically connecting said contact elements to said microchip, said microchip including means for transmitting a radio frequency signal which carries the heart signals detected by said contact elements.

55. A precordial strip assembly as in claim 54 wherein said elongate strip includes a reference contact element mounted thereon which serves as a common reference for each of said $V_1$ through $V_6$ conductive contact elements and is electrically connected to said microchip, said reference contact element being exposed on the first surface of said strip and being adapted to contact said patient's skin.

56. A precordial strip assembly as in claim 54 together with a reference contact element which serves as a common reference for each of said $V_1$ through $V_6$ conductive contact elements mounted on a patch, means electrically connecting said reference contact element to said microchip, said reference contact element being adapted to contact said patient's skin.

57. A precordial strip assembly as in claim 56 wherein said reference contact element is identified as the RL contact element and is adapted to contact said patient's skin near said right leg.

58. A precordial strip assembly as in claim 54 together with a conductive contact element identified as LA mounted on a patch, means electrically connecting said LA conductive contact element to said microchip, said LA conductive contact elements being adapted to contact said patient'skin near said left arm for detecting heart signals from said patient.

59. A precordial strip assembly as in claim 54 wherein said strip has first and second ends, together with a conductive contact element identified as LA mounted on said strip adjacent said first end and said $V_6$ conductive contact element, said conductive contact element being exposed on the first surface of said strip and being adapted to contact said patient's skin for detecting heart signals from said patient and being electrically connected to said microchip.

60. A precordial strip assembly as in claim 54 together with conductive contact elements identified as LL and RA mounted on said strip, means electrically connecting said LL and RA conductive contact elements to said microchip, said LL and RA conductive contact elements being exposed on the first surface of said strip and being adapted to contact said patient's skin near said right arm and left leg, respectively, for detecting heart signals from said patient.

61. A precordial strip assembly as in claim 54 together with LL and RA conductive contact elements mounted on first and second patches, means electrically connecting said LL and RA conductive contact elements to said microchip, said LL and RA conductive contact elements being adapted to contact said patient's skin near said right arm and left leg, respectively, for detecting heart signals from said patient.

62. A precordial strip assembly for use on a patient having a heart with a precordium lying thereover, skin and right and left arms and legs comprising an elongate strip having first and second surfaces, six conductive contact elements identified as $V_1$ through $V_6$ mounted in spaced apart positions along the length of said strip, said conductive contact elements being exposed on the first surface of said strip and being adapted to contact said patient'skin for detecting heart signals from said patient when said precordial strip assembly is placed on the precordium of the patient, junction means carried in a single region by said strip and electrically connected to said conductive contact elements and a microchip mounted on said strip in contact with said junction means, said microchip including means for transmitting a radio frequency signal which carries the heart signals detected by said contact elements.

63. A precordial strip assembly as in claim 62 wherein said microchip is detachably mounted to said strip.

64. A precordial strip assembly as in claim 62 wherein said strip has first and second ends, together with a conductive contact element identified as LA mounted on said strip adjacent said first end and said $V_6$ conductive contact element, said LA conductive contact element being exposed on the first surface of said strip and being adapted to contact said patient's skin for detecting heart signals from said patient and being electrically connected to said junction means.

65. A precordial strip assembly as in claim 62 together with conductive contact elements identified as LL and RA mounted on said strip, means electrically connecting said LL and RA conductive contact elements to said junction means, said strip including stretchable means to permit spacing of said LL and RA conductive contact elements between a first position in close proximity with said $V_1$ through $V_6$ conductive contact elements and a second position remote therefrom, said LL and RA conductive contact elements being exposed on the first surface of said strip and being adapted to contact said patient's skin near said right arm and left leg, respectively, when in said second position and said precordial strip assembly is placed on the precordium of the patient.

66. A precordial strip assembly as in claim 62 together with LL and RA conductive contact elements mounted on said strip, means electrically connecting said LL and RA conductive contact elements to said junction means, said LL and RA conductive contact elements being exposed on the first surface of said strip and being adapted to contact said patient's skin near said right arm and left leg, respectively, for detecting heart signals from said patient.

67. A precordial strip assembly as in claim 62 wherein said elongate strip includes a reference contact element mounted thereon which serves as a common reference for each of said $V_1$ through $V_6$ conductive contact elements and is electrically connected to said junction means, said reference contact element being exposed on the first surface of said strip and being adapted to contact said patient's skin.

68. An electrode assembly for use on a patient having a heart in a body comprising a layer of insulating material having first and second surfaces, a sufficient number of conductive contact elements for obtaining a twelve-lead electrocardiogram mounted in spaced apart positions on said layer of insulating material, said contact elements being exposed on the first surface of said layer of insulating material and being adapted to contact said patient's body for detecting heart signals therefrom, a microchip mounted on said layer of insulating material and conductor means electrically connecting said contact elements to said microchip, said microchip including means for transmitting a radio frequency signal which carries the heart signals detected by said contact elements.

69. A self-contained electrode structure for use in a wireless patient monitoring system for receiving signals from the heart in a body of a patient comprising a layer of insulating material having first and second sides, a conductive element carried by said layer of insulating material and disposed on said first side of said layer of insulating material, a battery carried on said second side of said layer of insulating material, microchip amplifier and transmitter means carried on said second side of said layer of insulating material and being coupled to said battery and to said conductive element for receiving heart signals from the heart of the patient and for transmitting wireless signals in accordance with heart signals received whereby said conductive element has its own exclusive power supply and microchip amplifier and transmitter means.

70. A method of electrocardiographic monitoring on a patient having a body with a heart therein and a precordium lying over the heart comprising the steps of placing an electrode assembly on the precordium of said patient, said electrode assembly having an elongate strip with first and second surfaces and six conductive contact elements identified as $V_1$ through $V_6$ mounted in spaced apart positions along the length of said strip and a microchip mounted on said strip in electrical contact with said $V_1$ through $V_6$ conductive contact elements, placing conductive contact elements identified as LA, LL and RA and a reference contact element on the body of said patient in electrical contact with said microchip, detecting heart signals from said patient through said contact elements, processing the heart signals in said microchip to produce twelve-lead electrocardiogram signals and transmitting a radio frequency signal which carries said twelve-lead electrocardiogram signals.

71. An electrode assembly for use on a patient having a body comprising a plurality of layers of insulating material having first and second surfaces, a sufficient number of conductive contact elements for obtaining a twelve-lead electrocardiogram mounted on said layers of insulating material, at least one conductive contact element being mounted on each said layer of insulating material, said contact elements being exposed on the first surface of said layers of insulating material and being adapted to contact said patient's body for detecting heart signals therefrom, a microchip mounted on one of said layers of insulating material and conductor means electrically connecting said contact elements to said microchip, said microchip including means for transmitting a radio frequency signal which carries the heart signals detected by said contact elements.

72. A method of electrocardiographic monitoring on a patient having a body with a heart therein comprising the steps of selecting an electrode assembly having a sufficient number of conductive contact elements for producing a twelve-lead electrocardiogram and a microchip electrically connected to said contact elements, placing said electrode assembly on the body of said patient, detecting heart signals from said patient through said contact elements and transmitting from said microchip a radio frequency signal which carries the heart signals detected by said contact elements.

* * * * *